United States Patent [19]

Tenen et al.

[11] Patent Number: 5,502,176
[45] Date of Patent: Mar. 26, 1996

[54] MYELOID CELL SPECIFIC PROMOTER

[75] Inventors: Daniel G. Tenen, Boston; Heike L. Pahl, Cambridge; Timothy C. Burn, Bedford, all of Mass.

[73] Assignee: Beth Israel Hospital, Boston Association, Boston, Mass.

[21] Appl. No.: 49,283

[22] Filed: Apr. 14, 1993

Related U.S. Application Data

[63] Continuation-in-part of Ser. No. 20,465, Feb. 19, 1993, which is a continuation of Ser. No. 837,776, Feb. 13, 1992, abandoned.

[51] Int. Cl.$^6$ .......................... C07H 21/04; C12N 5/16; C12N 15/85
[52] U.S. Cl. .................. 536/24.1; 435/240.2; 435/320.1
[58] Field of Search ...................... 536/24.1; 435/240.2, 435/320.1

[56] References Cited

PUBLICATIONS

Fregien et al., GENE 48:1–11 (1986).
Morishita et al., J. Biol. Chem. 262(31):15206–15213 (Nov. 5, 1987).
Pahl, Heike L. et al., "Optimization of Transient Transfection into Human Myeloid Cell Lines Using a Luciferase Reporter Gene", *Exp. Hematol.* 19:1038–1041 (1991).
Arnaout, M. Amin et al., "Amino Acid Sequence of the Alpha Subunit of Human Leukocyte Adhesion Receptor Mol (Complement Receptor Type 3)," *J. of Cell Biology* 106:2153–2158 (1988).
Shelley, C. Simon et al., "The promoter of the CD11b gene directs myeloid–specific and developmentally regulated expression," *Proc. Natl. Acad. Sci. USA* 88:10525–10529.
Pahl, H. L. et al., "Characterization of the Myeloid–Specific CD11b Promoter," *Blood* 79(4):865–870 (1992).
Pahl, H. L. et al., "The CD11B Promoter Directs Monocytic expression fo a Reporter Gene in Transgenic Mice," *The American Society of Hematology*, 33rd Annual Meeting, ASH Abstract (1991).

*Primary Examiner*—Stephanie W. Zitomer
*Attorney, Agent, or Firm*—Hamilton, Brook, Smith & Reynolds

[57] ABSTRACT

The subject application is drawn to a method of transfecting a myeloid cell line and a method of producing a selected product in a myeloid cell. The invention also includes myeloid cell specific promoters and enhancers, and constructs which contain these promoters and enhancers. The invention further includes a myeloid cell specific promoter-heterologous gene construct, where the expression of the heterologous gene is under the control of the myeloid cell specific promoter. The invention also includes a transgenic non-human mammal in which myeloid cells express a protein encoded by a heterologous gene. Finally the invention includes a method for identifying factors that can regulate myeloid cell specific transcription.

6 Claims, 12 Drawing Sheets

```
-412        AT TTTTTGTAG AGACAGGGTC TCTCTATGTT GCCCAGGCTG GTTTCAAACT

-360  CCCAGGCTCA AGCAATCCTC CTGCCTTGGC CTCCCAAAGT GCTGGCATTA CAGGCGTGAG

-300  CCACTGCGCC TGGCCCGTAT TAATGTTTAG AACACGAATT CCAGGAGGCA GGCTAAGTCT

-240  ATTCAGCTTG TTCATATGCT TGGGCCAACC CAAGAAACAA GTGGGTGACA AATGGCACCT

-180  TTTGGATAGT GGTATTGACT TTGAAAGTTT GGGTCAGGAA GCTGGGGAGG AAGGGTGGGC
                                                            PU.1

-120  AGGCTGTGGG CAGTCCTGGG CGGAAGACCA GGCAGGGCTA TGTGCTCACT GAGCCTCCGC
                            sp1                                    sp1

-60  CCTCTTCCTT TGAATCTCTG ATAGACTTCT GCCTCCTACT TCTCCTTTTC TGCCCTTCTT
                             gata
       *

+1   TGCTTTGGTG GCTTCCTTGT GGTTCCCTCA GTGGTGCCTGC AACCCCTGGT TCACCTCCTT

+61   CCAGGTTCTG GCTCCTTCCA GCCATGGCTC TCAGAGTCCT TCTGTTAACA Ggtgcatgggg... →
                             M  A  L  R  V  L   L  L  T   A  intron 1
```

CTTCTGCCTCCTACTTCTCCTTTTCTGCCCT

GAAGACGAGGATGAAGAGGAAAAGACGGGA

| Construct | Sequence | % Change From Wild Type Sequence |
|---|---|---|
| CD11b-95/-85 wild type | GACCAGGCAG | |
| CD11b-95/-85 linker scan | GGATCCCAGA | 90% |
| CD11b-85/-75 wild type | GGCTATGTGC | |
| CD11b-85/-75 linker scan | GGATCCCAGA | 60% |
| CD11b-75/-65 wild type | TCACTGAGCC | |
| CD11b-75/-65 linker scan | GGATCCCAGA | 90% |
| CD11b-65/-55 wild type | TCCGCCCTCT | |
| CD11b-65/-55 linker scan | GGATCCCAGA | 70% |
| CD11b-55/-45 wild type | TCCTTTGAAT | |
| CD11b-55/-45 linker scan | GGATCCCAGA | 90% |
| CD11b-45/-35 wild type | CTCTGATAGA | |
| CD11b-45/-35 linker scan | GGATCCCAGA | 60% |
| CD11b-35/-25 wild type | CTTCTGCCTC | |
| CD11b-35/-25 linker scan | GGATCCCAGA | 90% |
| CD11b-25/-15 wild type | CTACTTCTCC | |
| CD11b-25/-15 linker scan | GGATCCCAGA | 80% |
| CD11b-15/-5 wild type | TTTTCTGCCC | |
| CD11b-15/-5 linker scan | GGATCCCAGA | 80% |

FIGURE 9

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 533 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATTTTTTTGT  AGAGACAGGG  TCTCTCTATG  TTGCCCAGGC  TGGTTTCAAA  CTCCCAGGCT       60

CAAGCAATCC  TCCTGCCTTG  GCCTCCCAAA  GTGCTGGCAT  TACAGGCGTG  AGCCACTGCG      120

CCTGGCCCGT  ATTAATGTTT  AGAACACGAA  TTCCAGGAGG  CAGGCTAAGT  CTATTCAGCT      180

TGTTCATATG  CTTGGGCCAA  CCCAAGAAAC  AAGTGGGTGA  CAAATGGCAC  CTTTTGGATA      240

GTGGTATTGA  CTTTGAAAGT  TTGGGTCAGG  AAGCTGGGGA  GGAAGGGTGG  GCAGGCTGTG      300

GGCAGTCCTG  GGCGGAAGAC  CAGGCAGGGC  TATGTGCTCA  CTGAGCCTCC  GCCCTCTTCC      360

TTTGAATCTC  TGATAGACTT  CTGCCTCCTA  CTTCTCCTTT  TCTGCCCTTC  TTTGCTTTGG      420
```

| TGGCTTCCTT | GTGGTTCCTC | AGTGGTGCCT | GCAACCCCTG | GTTCACCTCC | TTCCAGGTTC | 480 |
| TGGCTCCTTC | CAGCCATGGC | TCTCAGAGTC | CTTCTGTTAA | CAGGTGCATG | GGG | 533 |

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AAAAGGAGAA G         11

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGGGAGGAAG GG         12

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGATCCCAGA         10

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAATTCAGAT C         11

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCGGTGACCC GGGAGATCTG AATTC         25

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTGACAAATG GCACCTTTTG GATAG    25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AAGTTTGGGT CAGGAAGCTG GGGAG    25

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGTCAGGAAG CTGGGGAGGA AGGGTG    26

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TTAACAGAAG GACTCTGAGA GCCAT    25

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TGGAAGGAGC CAGAACCTGG AAGGA    25

( 2 ) INFORMATION FOR SEQ ID NO:12:

( i ) SEQUENCE CHARACTERISTICS:
        ( A ) LENGTH: 27 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

GAAGGAGCCA GAACCTGGAA GGAGGTG                    27

( 2 ) INFORMATION FOR SEQ ID NO:13:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

GCTCAAAGAA GGGCAGAAAA GGAGAAGTAG G               31

( 2 ) INFORMATION FOR SEQ ID NO:14:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:14:

GCTCAAAGAA GGGCAGCCCG GGAGAAGTAG G               31

( 2 ) INFORMATION FOR SEQ ID NO:15:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:15:

GCTCAAAGAA GGGCAGAAAA GTCGACGTAG G               31

( 2 ) INFORMATION FOR SEQ ID NO:16:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:16:

GCTCAAAGAA GGGCAGAAAA GCTGCAGTAG G               31

( 2 ) INFORMATION FOR SEQ ID NO:17:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:17:

GGAAGCTGGG GAGGAAGGGT GGGCAGGCTG 30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

ACCTTCCTAT CAGAAAAAAA GGGGAAGCGA 30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

ACCTTCCTAT CAGAAAAACC CGGGAAGCGA 30

( 2 ) INFORMATION FOR SEQ ID NO:20:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CTTCTGCCTC CTACTTCTCC TTTTCTGCCC TGAAGACGGA GGATGAAGAG GAAAAGACGG 60

GA 62

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

TGCTCACTGA GCCTCCGCCC TCTTCCTTTG 30

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

TGCTCACTGA GCCTCCGAGC TCTTCCTTTG 30

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CCTGCCTGGT CTTCCGCCCA GGACTGCCCA    30

( 2 ) INFORMATION FOR SEQ ID NO:24:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

AGAAACCCCG CCCACACCTC TGGCCCCACC CCTTCTTCA    39

( 2 ) INFORMATION FOR SEQ ID NO:25:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GACCAGGCAG    10

( 2 ) INFORMATION FOR SEQ ID NO:26:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GGCTATGTGC    10

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TCACTGAGCC    10

( 2 ) INFORMATION FOR SEQ ID NO:28:

( i ) SEQUENCE CHARACTERISTICS:

(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

TCCGCCCTCT                                                                                      10

(2) INFORMATION FOR SEQ ID NO:29:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:29:

TCCTTTGAAT                                                                                      10

(2) INFORMATION FOR SEQ ID NO:30:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:30:

CTCTGATAGA                                                                                      10

(2) INFORMATION FOR SEQ ID NO:31:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:31:

CTTCTGCCTC                                                                                      10

(2) INFORMATION FOR SEQ ID NO:32:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:32:

CTACTTCTCC                                                                                      10

(2) INFORMATION FOR SEQ ID NO:33:

(i) SEQUENCE CHARACTERISTICS:
    (A) LENGTH: 10 base pairs
    (B) TYPE: nucleic acid
    (C) STRANDEDNESS: single
    (D) TOPOLOGY: linear ( i i ) MOLECULE TYPE: DNA (genomic)

( x i ) SEQUENCE DESCRIPTION: SEQ ID NO:33:

TTTTCTGCCC    10

( 2 ) INFORMATION FOR SEQ ID NO:34:

( i ) SEQUENCE CHARACTERISTICS:
( A ) LENGTH: 240 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:34:

| AACTTTCAAA | CCCAGTCCTT | CGACCCCTCC | TTCCCACCCG | TCCGACACCC | GTCAGGACCC | 60 |
| GCCTTCTGGT | CCGTCCCGAT | ACACGAGTGA | CTCGGAGGCG | GGAGAAGGAA | ACTTAGAGAC | 120 |
| TATCTGAAGA | CGGAGGATGA | AGAGGAAAAG | ACGGGAAGAA | ACGAAACCAC | CGAAGGAACA | 180 |
| CCAAGGAGTC | ACCACGGACG | TTGGGGACCA | AGTGGAGGAA | GGTCCAAGAC | CGAGGAAGGT | 240 |

MYELOID CELL SPECIFIC PROMOTER

GOVERNMENT SUPPORT

The work described herein was supported in part by the National Institutes of Health Grant No. CA41456. The United States Government has rights in the subject invention.

RELATED APPLICATION

This application is a Continuation-In-Part of U.S. patent application Ser. No. 08/020,465 filed Feb. 19, 1993 which is a File Wrapper Continuation of Ser. No. 07/837,776 filed Feb. 13, 1992, now abandoned, the contents of which are incorporated herein by reference.

BACKGROUND OF THE INVENTION

Gene expression is accomplished by the transcription of genetic information from DNA to RNA and then the translation of RNA to protein molecules. In transcription, RNA molecules are synthesized by using the base sequence of one strand of DNA as a template in a polymerization reaction that is catalyzed by RNA polymerases. RNA polymerases bind to a DNA strand at particular sites called promoters.

Transcriptional regulation is one mechanism of controlling gene expression. Some promoters are competent to support initiation by RNA polymerase, although extraneous proteins may act to prevent the initiation process. In other cases, the polymerase itself is not adequate and ancillary proteins (e.g. transcription factors) are necessary for initiation to occur.

Hematopoiesis (i.e., blood cell development) involves complex transcriptional and translational controls. Pluripotent stem cells in the bone marrow divide to form committed precursor cells, which mature along distinct pathways. The different types of blood cells are produced in different numbers, and the production of each must be regulated individually to meet changing needs. An understanding of these controls is still very incomplete.

A central objective in the study of hematopoiesis is the isolation of factors governing cell commitment to differentiation along a specific lineage. In several other systems, transcription factors have been shown to play a role in cellular differentiation. More recently, transcription factors have also been implicated in normal myeloid (monocytic, neutrophilic) differentiation and in the etiology of myeloid leukemia.

Since the late 1970's, progress has been made toward the development of general methods for introducing cloned gene sequences into eukaryotic cells (e.g., mammalian cells). As a result, genetic therapies whereby heterologous genes are introduced into, and expressed by host cells, are now possible. However, to date, little is known about the factors governing cell commitment in hematopoiesis, in part because myeloid cells have proven difficult to genetically engineer. For example, most promoters, particularly retroviral promoters, become repressed after being introduced into myeloid cells. Therefore, heterologous genes which are under the control of heterologous promoters are not expressed.

SUMMARY OF THE INVENTION

The present invention relates to myeloid cell specific gene expression. The invention includes myeloid cell specific gene expression under the control of either a myeloid cell specific promoter or a myeloid cell specific enhancer or both.

The invention also includes a myeloid cell specific promoter comprising a promoter that controls the expression of a gene that is preferentially expressed in differentiated myeloid cells. A preferred myeloid cell specific promoter is the 1.7 kb sequence upstream of (5') of the CD11b gene. In particular, the present invention relates to portions of the 4.5 kb sequence that are sufficient to direct myeloid cell specific expression of a heterologous gene. Additionally, the invention includes constructs that contain DNA sequences sufficient to direct myeloid cell specific expression of a gene.

The present invention further relates to a myeloid cell specific promoter-heterologous gene construct, and to a myeloid cell specific enhancer-heterologous gene construct whereby the expression of the heterologous gene is under the control of the myeloid cell specific promoter, the myeloid cell specific enhancer, or both. In addition, the present invention relates to methods of producing a selected heterologous gene product in a myeloid cell. These methods include introducing into the myeloid cell a heterologous gene under the control of a myeloid cell specific promoter, or a myeloid cell specific enhancer, or both. The invention also includes cells produced by the methods described herein. Further, the invention relates to a method of expressing a selected heterologous gene product in myeloid cells of an individual, i.e., gene therapy. According to this embodiment, cells produced by the methods described herein are introduced into an individual, wherein they express a heterologous gene under transcriptional control of a myeloid cell specific promoter or myeloid cell specific enhancer, or both.

Further, the invention includes a transgenic non-human mammal in which myeloid cells express a protein encoded by a heterologous gene under transcriptional control of a myeloid cell specific promoter or myeloid cell specific enhancer, or both.

The invention further includes a method for identifying factors that can regulate myeloid cell specific transcription.

Finally, the invention relates, in one embodiment, to a method of transfecting a myeloid cell line which comprises contacting a suspension of the cells with a heterologous gene construct and exposing the cells to electroporation.

The present invention provides a means of insuring that a selected product, such as a diagnostic, therapeutic or prophylactic substance, is expressed from a specific myeloid cell type, in vivo. Therefore, the present invention is useful, for example, for gene therapy or to drive the expression of antiviral agents, such as anti-HIV constructs. The present method is also useful in research, for example, to test the effect of the specific expression of heterologous genes, such as oncogenes, in specific myeloid cell types. Cells of the present invention are also useful for screening compounds for their effect on myeloid cell specific gene expression.

BRIEF DESCRIPTION OF THE DRAWINGS

FIG. 1 shows sequence analysis data for the −412 bp CD11b promoter region (SEQ ID No: 1).

FIG. 9 depicts the sequence replacements (SEQ ID NO: 4 and SEQ ID NO: 25 through SEQ ID NO: 33) obtained in individual linker scanning mutations.

DETAILED DESCRIPTION OF THE INVENTION

Figure 2:
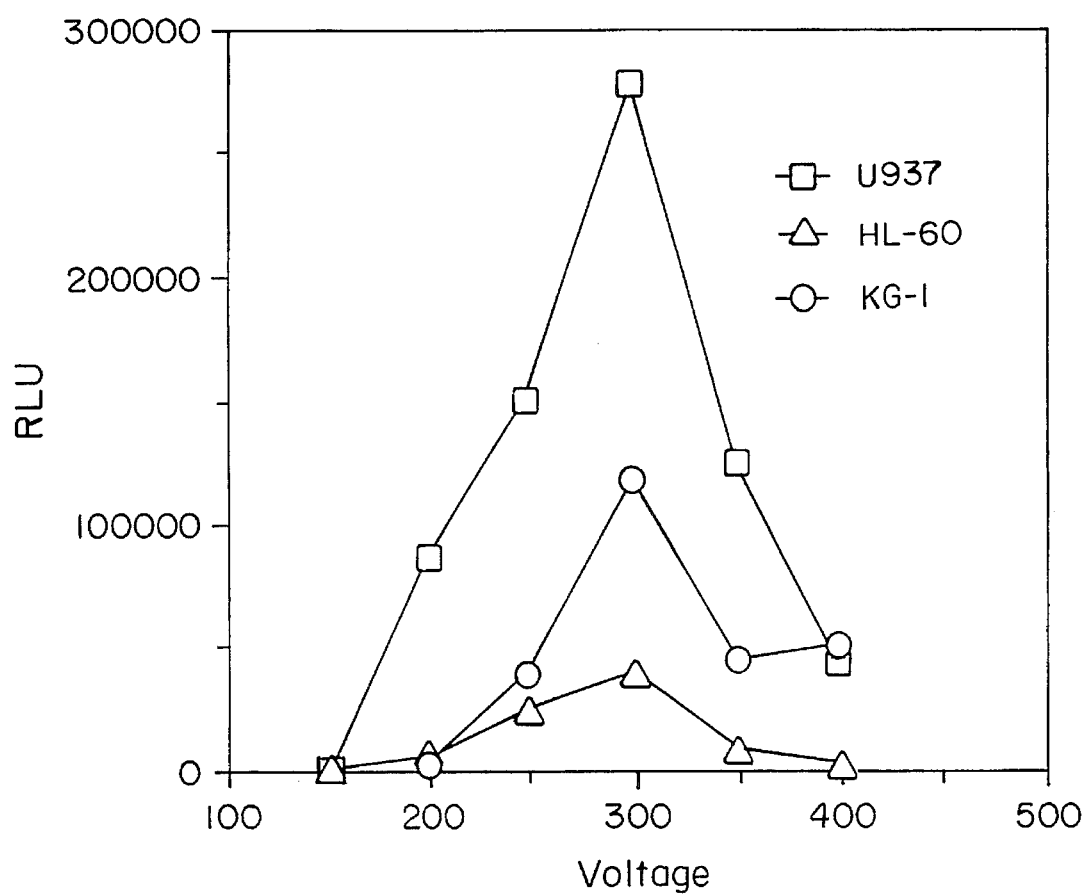
FIG. 2 depicts the effect of voltage on transfection of U937, HL-60, and KG-1 cells.

The present invention is based on the isolation of a myeloid cell specific promoter and the demonstration that this promoter directs myeloid specific expression of a heterologous gene in transient transfection assays in vitro, and in transgenic animals in vivo. The present invention is further based on the discovery that the first 92 bp of CD11b genomic flanking DNA are sufficient to direct high levels of tissue specific reporter gene activity. The invention is further based on the discovery that the transcription factor PU.1 binds at bp −20 of the CD11b promoter and that a functional PU.1 binding site is necessary for high level CD11b promoter activity.

The present invention, therefore, relates to a myeloid cell type specific promoter region comprising a promoter that controls the expression of a gene which is preferentially expressed in differentiated myeloid cells and not preferentially expressed in other cells of the myeloid lineage. In one embodiment of the invention, the myeloid cell type specific promoter is the CD11b promoter. In a preferred embodiment of the invention, the myeloid cell type specific promoter is present within the nucleic acid sequence depicted in FIG. 1 (SEQ ID NO: 1).

The invention also includes a myeloid cell type specific promoter whose sequence is substantially similar to, or substantially similar to a functional portion of, the nucleic acid sequence depicted at FIG. 1 and SEQ ID NO: 1. Additionally, the invention includes constructs which contain this promoter region, or portions thereof.

Further the invention includes an isolated nucleic acid strand that hybridizes to either a nucleic acid strand having the sequence listed above (SEQ ID NO: 1) or its complement, and constructs containing such isolated nucleic acid strands.

Additionally the application is drawn to a method of producing a selected product in a myeloid cell type. This is accomplished by introducing a heterologous gene under the control of a myeloid cell type specific promoter which encodes a selected product into myeloid cells. The preferred myeloid cell type specific promoter is the CD11b promoter.

The invention further includes a myeloid cell type specific promoter-heterologous gene construct, wherein expression of the heterologous gene is under the control of the myeloid cell type specific promoter. In a preferred embodiment the myeloid cell type specific promoter is the CD11b promoter.

The present invention also includes a transgenic non-human mammal in which myeloid cells express a protein encoded by a heterologous gene introduced, as a component of a myeloid cell-specific promoter-heterologous gene construct, into the pronucleus of an embryo from which a transgenic mammal, or an ancestor of a transgenic mammal, developed.

The present invention further includes a method for identifying factors which can regulate myeloid cell specific transcription. This is practiced by: 1) obtaining a myeloid cell which contains (e.g., has been transfected with, or is derived from a cell transfected with) a heterologous gene under the transcriptional control of a myeloid cell specific promoter (i.e., a myeloid cell promoter-heterologous gene construct); 2) contacting the cell containing the myeloid cell promoter-heterologous gene construct with a selected factor; 3) assaying for expression of the heterologous gene and comparing its expression in cells contacted with the factor with expression of the gene in cells not contacted with the factor, and thereby determining whether the expression pattern of the heterologous gene is altered in cells contacted with the factor as compared to that of cells which have not been contacted with the factor.

The present invention further relates to a method of transfecting a myeloid cell line which comprises contacting a suspension of the cells with a heterologous gene construct, and exposing the cells to electroporation. In one embodiment of the invention the heterologous gene construct is a plasmid. In another embodiment of the invention the electroporation is carried out at about 400–1,000 µF and about 200–450 V. In the preferred embodiment the electroporation is carried out at about 960 µF and about 300 V. The myeloid leukemic cell lines may include, but is not limited to, the HL-60, U937, and KG-1 cell lines. In the preferred embodiment, the plasmid is a promoterless luciferase vector, such as pXP2, with a cytomegalovirus (CMV) luciferase promoter inserted.

The present invention is based, in part, on the discovery of an efficient technique for transfecting myeloid cell lines, and the discovery that the human genomic region upstream of (5' of) the genomic region encoding CD11b comprises a 1.7 kb sequence which contains a control element(s) which is capable of directing myeloid specific transcription of a heterologous gene in transfected myeloid cells, but not capable of directing expression in lymphoid cells or epithelial cells.

As further described in the Examples, it is now possible to specifically express a heterologous gene in a myeloid cell type by introducing into a myeloid cell a heterologous gene under the control of a myeloid cell specific promoter. All myeloid cell types derive from a pluripotent self-renewing population of stem cells. These pluripotent cells can differentiate into either a lymphoid stem cell or a myeloid stem cell. Lymphoid stem cells further differentiate to ultimately produce B cells or T cells. Myeloid stem cells ultimately differentiate into erythrocytes, thrombocytes, monocytes (including macrophages) and granulocytes (e.g. basophils (including mast cells), eosinophils and neutrophils).

For the purposes of the subject invention, the phrase "myeloid cell type" or "myeloid cell" refers to monocytes, granulocytes (e.g., basophils, including mast cells), macrophages, NK cells, and precursor cells in these cell lineages.

As described herein, the phrase "myeloid cell specific promoter" or "myeloid specific promoter" refers to a DNA sequence which functions as a transcriptional control element or elements and which directs the expression of a gene which is expressed in myeloid cells and which is not expressed in other cell types. The term "myeloid cell specific promoter" can include all or a portion of a DNA sequence which functions as a transcriptional control element.

The term "functional portion" refers to DNA sequences which are of sufficient size and sequence to have the desired function (i.e. the ability to cause tissue specific expression of a heterologous gene).

A sequence which is "substantially similar" to another sequence is one which has a substantial degree of DNA or RNA sequence homology to the other sequence. A sequence which "hybridizes" with another is one which has sufficient nucleic acid sequence complementarily to allow the formation of base pairing and hydrogen bonding under standard DNA hybridization conditions.

The term "construct" includes linear or circular recombinant DNA sequences comprising a functional portion of the myeloid cell specific promoter and DNA encoding a heterologous gene. The myeloid cell specific promoter is functionally linked to the heterologous gene in the constructs described herein.

"Heterologous DNA" or "heterologous gene" refer to DNA sequences, or a gene, which are not normally present in the cell as obtained, or which are not ordinarily functionally associated with a myeloid cell specific promoter region in the cell as obtained, or which are not ordinarily functionally associated with a myeloid cell specific enhancer in the cell as obtained.

A myeloid cell specific promoter of the present invention can be obtained from a naturally-occurring source, or it can be produced using any of a variety of techniques, such as genetic engineering or cloning methods, PCR amplification or synthetic techniques. Although the promoter described herein is of human origin, myeloid cell specific promoters and enhancers can be derived from another source (or have the sequence of a myeloid cell specific promoter or enhancer of other than human origin), such as from murine origin.

The CD11b promoter is a strong promoter of expression in myeloid cells. Therefore, in addition to cell specific expression, the CD11b promoter offers the advantage of high level of expression of a desired product in myeloid cells.

The 5' upstream region of the CD11b gene contains information necessary for tissue specific expression of a heterologous gene. However, the 5' upstream region can be further characterized and divided into regulatory domains. For example, regulatory domains of a myeloid cell specific promoter, which modify transcriptional activity of neighboring regions, have been identified by transfecting the myeloid cell with DNA constructs containing varying lengths of the 5' upstream region and a heterologous gene and detecting alterations in expression of the heterologous gene. These identified regulatory domains of the 5' upstream region can be used to identify other myeloid cell specific promoters or myeloid cell specific enhancers.

Myeloid cell specific promoter or enhancer-heterologous gene constructs can be used to screen for and identify regulators of cell specific transcription. For example, myeloid cells may be transfected with DNA constructs containing functional portions of a myeloid cell specific promoter or enhancer and a heterologous gene in the presence of a variety of potential transcription factors; the ability of the transcription factors to alter the function of the promoter or the enhancer may then be tested by assaying for alterations in expression of the heterologous gene.

The following is a description of a myeloid type specific promoter and heterologous gene construct, comprising the CD11b promoter and the gene encoding luciferase. The Examples further demonstrate that DNA sequences represented in the region upstream of (5' of) the CD11b gene are capable of directing myeloid cell specific expression of a heterologous gene. Also described is a method for transfecting the construct into a number of myeloid cell lines and assaying the expression of the heterologous luciferase gene. All of the references listed in parenthesis are intended to be incorporated by reference.

CD11b, the alpha subunit of the CD11b/CD18 heterodimer, is an integrin cell surface receptor whose expression is tightly regulated in both a developmental and a tissue specific manner. CD18, the beta subunit, is expressed on all leukocytes in combination with one of the three CD11 alpha subunits; however, the CD11b/CD18 heterodimer (previously referred to as Mac-1 or Mo-1) is expressed exclusively on the surface of mature monocytes, macrophages, neutrophils and natural killer (NK) cells, reflecting the more restricted tissue distribution of CD11b. Immature precursor cells do not express the antigen on their surface, and undifferentiated myeloid leukemic lines such as HL-60 and U937 cells show little or no detectable CD11b mRNA. In addition, CD11b mRNA is up-regulated in myeloid cell lines induced to differentiate in vitro.

Results presented herein demonstrate that CD11b mRNA is only present in cells expressing the CD11b antigen, indicating that the tissue specificity of CD11b expression is transcriptionally regulated. Two different inducing agents, TPA and retinoic acid, unregulate the rate of CD11b transcription in U937 and HL-60 cells. Increases in CD11b transcriptional rates correlate with increased steady state levels of mRNA as measured by Northern blot analysis and antigen expression measured by fluorescence-activated cell sorting (FACS) (Rosmarin A. G. et al., *Blood* 73:131 (1989)). In addition, nuclear run-on experiments using HL-60 myeloid cells, uninduced and induced with $10^{-7}$M 12-O-tetradecanoyl-phorbol-13-acetate (TPA) for 48 hours, demonstrate that the up-regulation is predominantly transcriptional. The 5' upstream CD11b genomic region, including a 1.7 Kb sequence which directs myeloid-specific transcription of a heterologous gene, has been isolated.

A 1.7 Kb Hind III fragment from the region upstream of (5' of) the gene encoding CD11b, linked to a luciferase reporter gene, was transiently transfected into the myeloid cell lines U937 and HL-60, and into the non-myeloid cell lines Jurkat T, Raji B and Hela, as described in detail in Example 1. The myeloid cell lines HL-60 and U937 are refractory to transfection by calcium phosphate or DEAE dextran. However, the method set forth in Example 1 optimizes the transient transfection of myeloid cell lines using electroporation and the firefly luciferase reporter gene, which requires only 8 to 14 hours between transfection and data analysis.

The luciferase assay is extremely sensitive; transcription which is not detectable by Northern blot or nuclear run-on assays can be measured with this system. The system was used in combination with the inducing agent TPA, thus allowing analysis of the developmentally regulated CD11b gene in these cells. The results of the transient transfection assay reflect the activity of the myeloid cell specific promoter as measured in relative light units (RLU) produced by expression of the heterologous gene product, luciferase. These results are presented in Table 1.

TABLE I

Myeloid Specific Expression of the CD11b Promoter In Vitro

|  | PXP2 | CD11b | CMV |
| --- | --- | --- | --- |
| myeloid |  |  |  |
| U937 |  |  |  |
| uninduced | 293 | 75,097 | 4,038,451 |
| induced w/3 × 10⁻⁸ M TPA | 605 | 590,585 | 162,717,980 |
| HL-60 |  |  |  |
| uninduced | 285 | 7,161 | 25,188 |
| induced w/3 × 10⁻⁸ M TPA | nd | 140,242 | nd |
| non myeloid |  |  |  |
| Jurkat T |  |  |  |
| uninduced | 302 | 1,376 | 2,585,656 |
| induced w/3 × 10⁻⁸ M TPA | nd | 4,165 | 37,192,920 |
| Raji B |  |  |  |
| uninduced | 320 | 11,135 | 5,445,734 |
| induced w/3 × 10⁻⁸ M TPA | nd | nd | nd |
| HeLa |  |  |  |
| uninduced | 287 | 510 | 793,637 |
| induced w/3 × 10⁻⁸ M TPA | nd | nd | nd |

("nd" = not done)

These data demonstrate that the CD11b promoter directs myeloid-specific transcription of a reporter luciferase gene (i.e., a heterologous gene) in transfected HL-60 and U937 myeloid cells, but not in the Jurkat T cell line. Luciferase expression in the myeloid cell lines is increased when the cells are induced to differentiate with the phorbol ester TPA.

Tissue specific gene expression may be regulated either by tissue specific activating proteins or by repression of expression in appropriate cell types (Baniahmad A. et al., *J. Cell Biol.* 6:2297 (1987)). Deletion analysis of the CD11b promoter indicates the presence of multiple positive regulatory elements. These elements, as well as the basal promoter, are likely to be tissue specific, as these constructs are very active in U937 cells but not in HeLa cells.

Results herein presented indicate the presence of myeloid specific in vitro DNA binding activities in the first 92 bp of the promoter. Interestingly, the sequence between bp −169 and bp −92 (FIG. 7) contains the purine rich sequence which presents potential binding sites for members of the ets superfamily of genes (Karim F. D. et al., *Genes Dev.* 4:1451 (1990); Galson D. L. et al., *Mol. Cell Biol.* 381 (1988)). PU.1 (Spi-1) is a member of this family and is expressed exclusively in monocytes and B cells (Klemsz M. J. et al., *Cell* 61:113 (1990)).

Figure 7:
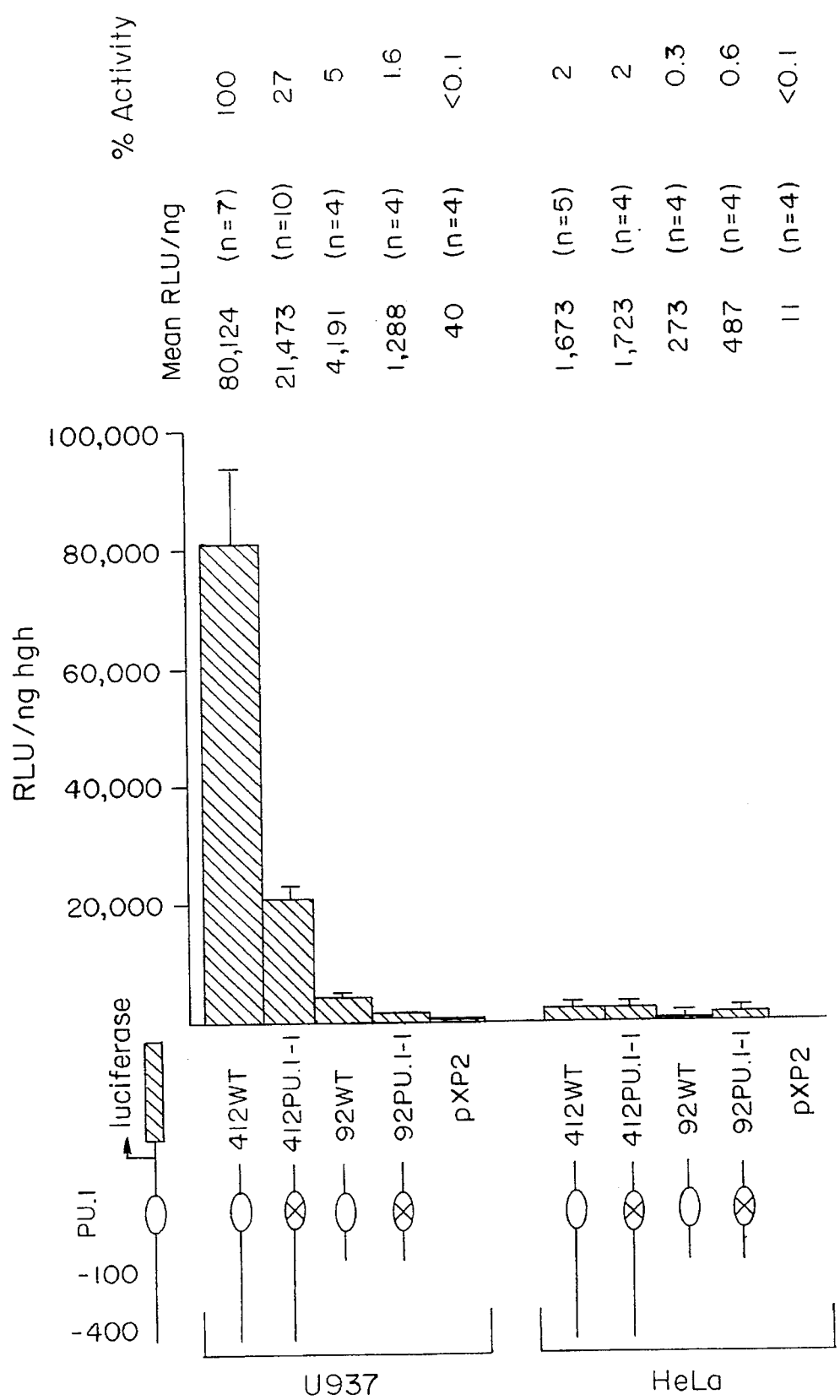
FIG. 7 is a comparison of the ability of wild type and mutant CD11b promoter to direct reporter gene activity in transient transfection assays.

Data herein presented also show that the GATA site at bp −40 in the CD11b promoter is not functional in U937 cells or that it functions redundantly in combination with another site which must also be destroyed in order to reduce promoter function. Furthermore, Shapiro et al. (Shapiro L. H. et al., *J. Bio. Chem.* 266:11999 (1991)) noted that the sequence CCCTTCC is found in several myeloid specific promoters, such as myeloperoxidase (Morishita K. et al., *J. Bio, Chem.* 262.:15208 (1987)), cathepsin G (Hohn P. A. et al., *J. Bio. Chem*, 264:13412 (1989)), c-fes (Greer P. et al., *Mol. Cell Biol*, 10:2521 (1990)), and CD13 (Shapiro L. H. et al., *J, Bio. Chem.* 266:11999 (1991)). This sequence is also found in the CD11b promoter, on the antisense strand at bp −132 (FIG. 7). Interestingly, on the sense strand, these nucleotides overlap with the potential PU.1 binding site. A second sequence noted by Hohn et al. (Hohn P. A. et al., *J. Bio. Chem.* 264:13412 (1989)), and Shapiro et. al. (Shapiro L. H. et al., *J. Bio, Chem,* 266:11999 (1991)), to be present in myeloid promoters (CCCCACCC or the related CCCCTCCC) is not present in the CD11b promoter.

A fragment extending from bp −1704 to bp −76 does not enhance transcription from an enhancerless tk promoter, nor does a fragment extending from bp −1704 to bp −265 activate an enhancerless MMTV promoter (Nordeen S. K., *BioTechniques* 6:454 (1988)). Thus, this DNA fragment does not contain a classical enhancer.

Repressors and silencers also play a role in the regulation of CD11b expression. Deletion analysis (FIG. 6) indicates the presence of a negative regulatory element between bp −1287 and bp −654. However, this element does not behave as a classical silencer element in that it will not repress transcription from a heterologous (tk) promoter (Nordeen S. K., *BioTechniques* 6:454 (1988)).

In addition to enabling the isolation of myeloid transcription factors, the identification of a myeloid promoter that directs tissue specific transcription in vivo enables targeting of heterologous gene expression to a specific cell type. Results obtained with the 1.7 kb CD11b promoter operatively linked to a Thy 1.1 reporter gene in transgenic mice demonstrate that this promoter drives high level expression of the transgene in mouse peripheral blood monocytes (Pahl H. L. et al., *Blood* 78:373a (1991).

Myeloid cell type specific promoter-heterologous gene constructs according to the present invention are useful for the expression of proteins in specific mammalian cell types. Therefore, the present invention is useful, for example, for gene therapy. An example of this use would be the treatment of blood disorders, such as some leukemias, in which the expression of an abnormal gene, or the failure to express a normal gene, results in a disease state. Such disorders can be treated by introducing into the host's cells DNA constructs which include a copy of the normal gene operatively linked to a myeloid cell specific promoter. The DNA construct can be introduced into host cells by transfection in situ. Alternatively, host cells can be removed from the host prior to introduction of the DNA construct, and then the transfected cells or their progeny can be returned to the host.

A particular example of a leukemia potentially treatable by this method is acute promyelocytic leukemia (de Thè, H. et al., *Nature* 347:558–561 (1990); Kakizuka, A. et al., *Cell* 66:663–674 (1991)). Patients with this disease express both an abnormal retinoic acid receptor and a normal (i.e., normally functioning) retinoic acid receptor. However, the abnormal gene product is dominant and overcomes the normal phenotype. Gene therapy could be used, for example, to introduce additional copies of the gene encoding a normally functioning retinoic acid receptor operatively linked to a myeloid cell type specific promoter. It is possible that increased expression of genes encoding normally functioning retinoic acid receptors in myeloid cells can overcome the disease state caused by expression of the abnormal retinoic acid receptor.

Another use for tissue specific regulatory elements embraced by the present invention is for driving the expression of antiviral agents, such as antisense RNA constructs, ribozymes, or trans-dominant mutants, in a tissue specific manner. For example, because a major resevoir of the HIV virus is in monocytes, a myeloid specific promoter can be used to drive the expression of anti-HIV constructs in monocytic cells but not in other cell types. Myeloid cell type specific promoters are also useful in research, for example, to analyze the effect of the specific expression of heterologous genes, such as oncogenes, in specific myeloid cell types.

The myeloid cell type specific promoter-heterologous gene construct can be introduced into an animal at an embryonic stage. For example, the construct can be introduced into the pronuclei of fertilized eggs which are reimplanted into a female and maintained under appropriate conditions for development. The resulting offspring contain the heterologous gene, which is expressed in specific myeloid cell types.

Alternatively, the myeloid cell type specific promoter-heterologous gene construct can be introduced into the bone marrow of an individual (e.g. prior to bone marrow transplantation) so that a specific myeloid cell type expresses the heterologous gene.

This invention is illustrated further by the following Examples:

Example 1 - Method for Assaying Myeloid Cell Type Specific Expression Cell Culture HL-60 (ATCC # CCL 240), U937 (ATCC # CRL 1593), KG-1 (ATCC # CCL 246), Jurkat T, Raji B, and the HeLa cells were maintained in RPMI 1640 (GIBCO) supplemented with 10% fetal calf serum (Hyclone) and 2 mM 1-glutamine (Gibco). Cells were maintained between $10^5$/ml and $10^6$/ml.

Transfections

Cells were split to $10^5$/ml 16–24 hours prior to transfection. At the time of transfection, cells were harvested by centrifugation at 500×g for 5 minutes at room temperature (RT). Cells were washed twice with RPMI, containing neither fetal calf serum nor 1-glutamine, at RT. Cells were resuspended at 2.8×$10^7$/ml in RPMI, and 0.5 ml of cell suspension placed into a 0.4 cm electroporation cuvette (BioRad). Twenty µg of supercoiled plasmid DNA in water were dried under vacuum, dissolved in 50 µl of RPMI, and added to the cell suspension in the cuvette.

Reporter gene activity is roughly proportional to the amount of plasmid transfected. The amount of plasmid necessary for satisfactory analysis is that which results in reporter gene activity of about 100 fold above background (30,000 RLU). Cells and plasmid were incubated for 5 minutes at RT prior to electroporation at 960 µF and various voltages (BioRad gene pulser).

The cuvettes were transferred to an ice bath for 15 minutes immediately after transfection. The cells were then transferred to 10 ml of RPMI 1640 containing 10% fetal calf serum and 2mM 1-glutamine at RT. For inductions, 5 ml (7×$10^6$ cells) were removed to a 100 mm tissue culture dish, diluted to 2.3×$10^5$ cells/ml, and 3 ×$10^{-8}$M TPA (Sigma, diluted in RPMI from a stock solution of $10^{-3}$M TPA in DMSO) was added. Cells were harvested for luciferase assays at various times post-transfection.

Luciferase Assays

Cell lysis and luciferase assays were performed as described by Brasier et al., *Biotechniques* 7:1116 (1989) with modifications: cells were harvested by centrifugation at 500×g for 5 minutes at RT and washed once with Dulbecco's PBS (Sigma) at RT. 7×$10^6$ cells were lysed in 500 µl of 25 Mm glycyl glycine [pH 7.8], 15 Mm MgSO$_4$, 15 Mm KPO$_4$ [pH 7.8], 4mM EGTA [pH 7.8], 1 Mm DTT, and 1% Triton X-100 at RT. The lysates were transferred to 1.5 ml Eppendorf tubes, vortexed for 2 minutes at RT and centrifuged for 5 minutes at 12,000 g at 4° C.

The supernatant was assayed for luciferase activity by adding 100 µl of supernatant to 300 µl of assay buffer (25 mM glycyl glycine [pH 7.6], 15 mM MgSO$_4$, 15 mM KPO$_4$ [pH 7.8], 4 mM EGTA [pH 7.6], 1 mM DTT and 1 mM ATP) and measuring light emission in a model 2010 Analytical Bioluminescence Luminometer. The liuminometer was programmed to inject 100 µl of luciferin (0.3 mg/ml) and measure light emission for 30 seconds after injection. Output is quantitated as relative light units, RLU. Cell lysates can be stored at –80° C. for several weeks without detectable loss of luciferase activity.

Luciferin (Analytical Bioluminescence Laboratories, potassium salt) was prepared as a 0.3 mg/ml solution in water and stored in 10 µl aliquots at –20° C. in the dark.

Growth Hormone Assay and Cotransfections

Human growth hormone concentration in media of transfected cells was measured by radioimmunoassay (Nicol's Institute) according to manufacturer's specification except as noted below. Cotransfections were performed as follows: cells were maintained in RPMI with serum as noted above, but after harvesting were washed twice in Iscove's Modification of Dulbecco's Media (IMDM) (Gibco), electroporated in IMDM and then resuspended at 7 ×$10^5$/ml in IMDM +10% fetal calf serum and 2 mM 1-glutamine. For induction, cells were diluted to 2.3× $10^5$/ml and treated with 3×$10^{-8}$ M TPA in IMDM+10% fetal calf serum +2 mM 1-glutamine. At 14 hours post transfection, the cells were harvested by centrifugation at 500× g at room temperature. The cell pellet was assayed for luciferase activity as described above. The supernatant media was assayed for human growth hormone following the manufacturer's instructions.

Plasmids

All plasmids were prepared by alkaline lysis and CsCl density gradient centrifugation (Maniatis T. et al., Cold Spring Press (1982)). The cytomegalovirus (CMV) luciferase plasmid was constructed by inserting a CMV promoter (provided by Dr. Sunyoung Kim) into pXP2 (Nordeen S. K., *Biotechniques* 6:454 (1988)). The CMV human growth hormone plasmid consisting of the CMV promoter driving expression of a functional human growth hormone coding sequence, was provided by Dr. Leonard Zon.

Results

The Effect of Voltage on Transfection Efficiency

The effect of voltage on transfection of U937, Hl-60 and KG-1 cells is depicted in FIG. 2. Twenty micrograms of CMV luciferase was transfected at the voltages indicated, and luciferase activity was measured in relative light units (RLU) was assayed 16 hours after transfection. The values for U937 have been divided by 10, and the background for the promoterless luciferase vector alone (pXP2) was <400 RLU at each point.

Reporter gene activity peaks sharply at 300V for U937, HL-60, and KG-1 cells. Differences of 50V can result in ten-fold decreased reporter gene activity and optimal voltage differs between cell lines. For example, the Jurkat T cell line transfects optimally at 250 volts. Thus each cell line used must be tested individually for optimal transfection conditions.

The Effect of Plasmid Concentration on Transfection Efficiency

Figure 3:
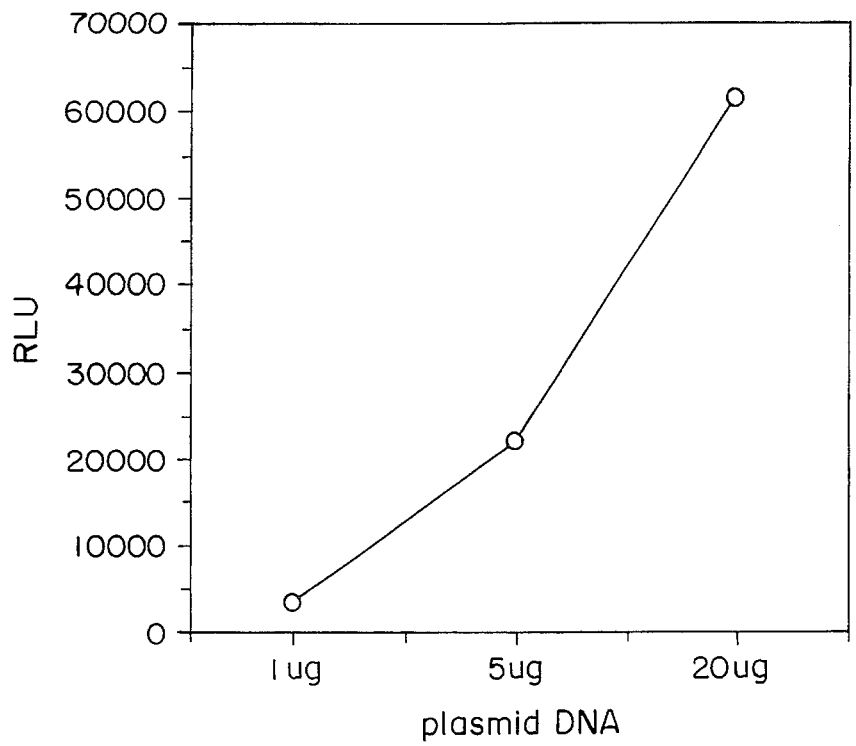
FIG. 3 depicts the effect of DNA concentration on reporter gene activity in U937 cells.

U937 cells were transfected with 1 µg, 5 µg or 20 µg of RSV luciferase plasmid at 300 V and 960 µF and luciferase activity was assayed 16 hours post transfection. The results of this assay are shown in FIG. 3. In this Figure, RLU indicates luciferase activity in relative light units. The background for the promoterless luciferase vector alone (pXP2) was <400 RLU at each DNA concentration shown.

Reporter gene activity was roughly proportional to the amount of plasmid transfected. This relationship can be used to gauge the amount of plasmid necessary for satisfactory analysis, because reporter gene activity 100 fold above background (30,000 RLU) should be sufficient for most analysis.

Time Course of Luciferase Activity in Transfected Cells

Figure 4:
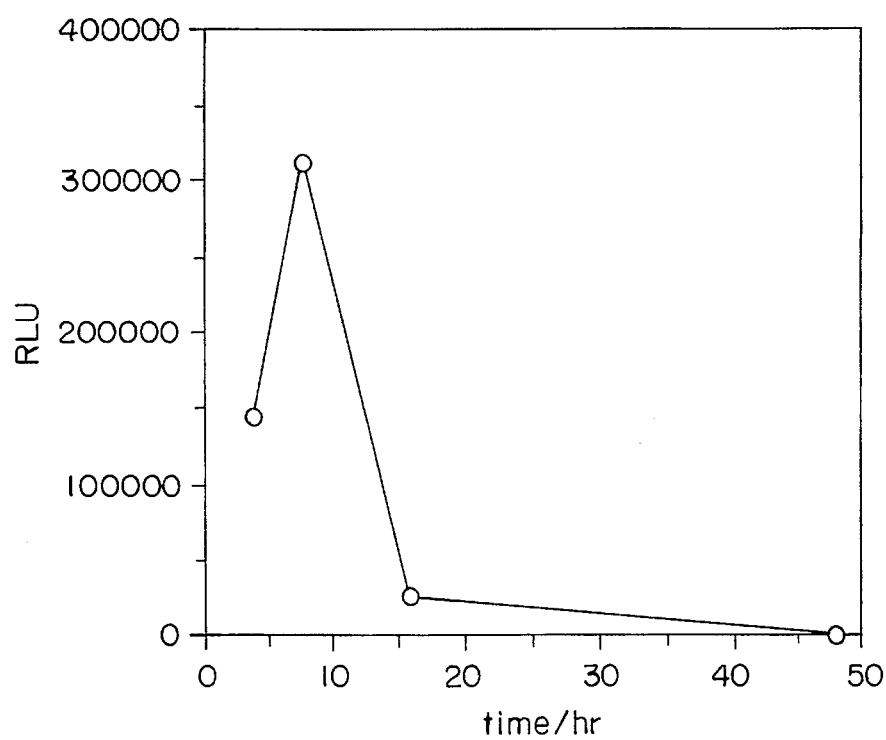
FIG. 4 shows the effect of time on luciferase activity in electroporated U937 cells.

The rate of cell recovery after transfection, the rate of transcription from a given promoter, and mRNA stability may influence the time course of reporter gene expression in a given transfection system. To optimize reporter gene activity in this system, 20 µg of RSV luciferase plasmid were transfected into U937 cells by electroporation at 300 V and 960 µF and luciferase activity was assayed at 4, 8, 16 and 48 hours following transfection. The background for the promoterless luciferase vector pXP2 was <400 RLU at each point. Again, a very sharp peak of activity was seen at 8 hours post transfection (FIG. 4). By 16 hours the activity had decreased to one-tenth of the activity observed at 8 hours, but was still 60 fold above background.

Figure 5:
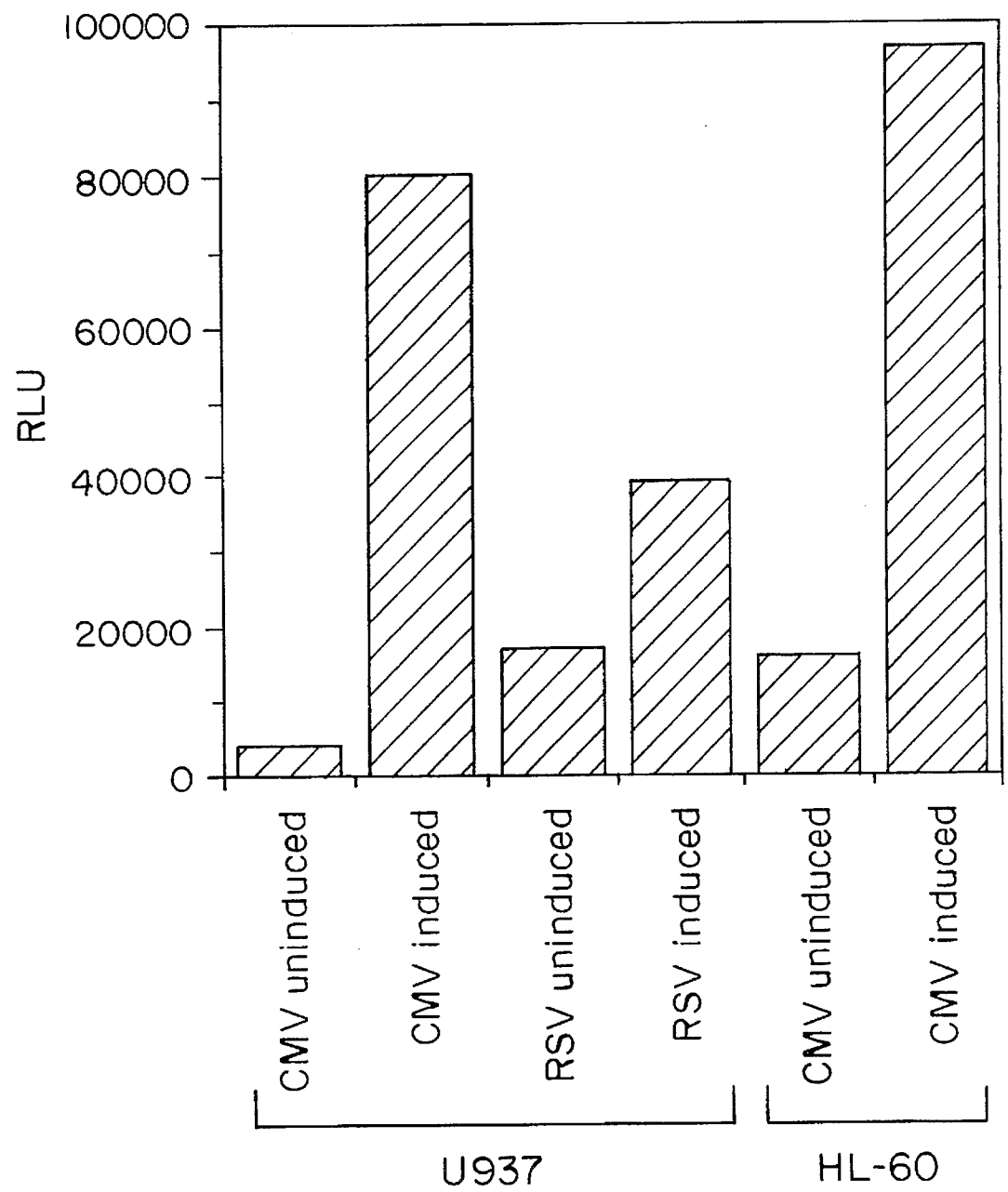
FIG. 5 is a bar graph depicting the effect of TPA on reporter gene activity in U937 and HL-60 cells.

The CMV and RSV promoters were both inducible by TPA stimulation, but to greatly varying degrees, as shown in FIG. 5. Twenty micrograms of CMV luciferase or RSV luciferase was transfected into U937 or HL-60 cells and half the cells were induced with $3 \times 10^{-8}$ M TPA. Luciferase activity was assayed 16 hours after transfection. In FIG. 5, values for the CMV construct in U937 cells have been divided by 100. The background for the promoterless luciferase vector alone (pXP2) was <400 RLU at each point.

While the RSV promoter only increased reporter gene activity twofold after TPA treatment, the CMV promoter in both U937 and HL-60 cells was induced 7 to 20 fold upon treatment with TPA.

Internal Control for Transfection Efficiency

Because transformation efficiency varies slightly between separate transfections performed under identical conditions, a standard is needed as an internal control. Therefore, 2 µg of the CMV human growth hormone construct were used in cotransfection experiments.

The human growth hormone radioimmunoassay relies on an avidin biotin interaction; we found that the concentration of biotin in RPMI (2 mg/L), even when diluted according to the manufacturer's specifications, resulted in large interassay variability. Therefore, we have modified our transfection protocol as noted above, replacing RPMI with IMDM. Under these conditions the assay is reproducible and linear with respect to human growth hormone levels between 0.5 and 50 ng/L.

In U937 cells, cotransfection of 2 µg CMV human growth hormone plasmid generated approximately 5 ng human growth hormone per liter when 100 µl of the supernatant media was assayed 14 hours post transfection. Because human growth hormone is secreted into the media, it constitutes an ideal control: no cell lysate need be sacrificed for measuring the internal transformation control.

Sensitivity of the Luciferase Assay

Both RSV and CMV are strong viral promoters; i.e., they direct more transcription than most cellular promoters. Therefore, to test the sensitivity of the system, a cellular promoter of the CD11b gene was used. CD11b transcripts cannot be detected in uninduced HL-60 cells either by Northern blot or by run-on transcription (Rosmarin A. G., et al., *Blood* 73:131 (1989)). This promoter was strongly upregulated by the addition of TPA to these cells (Rosmarin A. G., et al., *Blood* 73:131 (1989)).

Twenty µg of CD11b promoter plasmid were transfected into HL-60 cells at 250V, 960 µF, and $7 \times 10^6$ cells induced with $3 \times 10^{-8}$ M TPA. Cells were harvested 14 hours post transfection. Transcription in uninduced HL-60 cells was 7161 RLU, 25-fold above background (luciferase vector pXP2 without promoter), and was induced 20 fold to 140,242 RLU by induction with TPA (Table I).

Example 2 - Myeloid Specific Expression of the CD11b Promoter In Vitro

Expression of CD11b mRNA is Tissue Specific

Total cellular RNA was isolated and CD11b Northern blot analysis performed as described (Rosmarin A. G. et al., *Blood* 73:131 (1989)) from the following cells: HeLa (ATCC # CCL 2), human primary foreskin fibroblasts, K562 (ATCC # CCL 243), KG-1 (ATCC # CCL 246), HL-60 (ATCC # CCL 240), Laz509, Jurkat, fetal human thymocytes, human peripheral blood monocytes. HL-60 cells were induced with TPA and DMSO as described (Rosmarin A. G. et al., *Blood* 73:131 (1989)). Equivalent RNA loading (10 µg/lane) was confirmed by visual inspection of ethidium bromide staining of ribosomal bands and by hybridization with a 28S ribosomal RNA probe (Toothaker L. E. et al., *Blood* 78.:1826, (1991)).

Northern analysis of RNA from several cell lines as well as normal thymus and peripheral blood monocytes shows the presence of CD11b mRNA only in induced myeloid cell lines and peripheral blood mononuclear cells. The Northern was probed with a 1.9 kb XbaI fragment of the CD11b cDNA; (Arnaout M. A. et al., *J. Cell Biol.* 06:2153 (1988)), and the blot was exposed for 18 hours with an intensifying screen at $-80°$ C. Very low levels of CD11b mRNA were detected in K562 cells, which are derived from a patient with CML and show some characteristics of granulocytic cells. (Klein E., et al., *Int. J. Cancer* 18:421 (1976)). Therefore, CD11b mRNA expression parallels the presence of surface antigen. (Rosmarin A. G. et al., *Blood* 73:131 (1989); Knapp W. (ed), Leukocyte Typing IV: White Cell Differentiation Antigens. New York, N.Y., Oxford University Press, 1989 (suggesting that tissue specific expression of CD11b may be controlled at the mRNA level)).

Transcriptional Regulation of CD11b Expression

In order to determine whether CD11b is transcriptionally regulated, nuclear run on assays were performed on uninduced HL-60 and U937 cells as well as cells induced for 24 hours with $10^{-7}$ M TPA (HL-60 and U937) or 6 days with $10^{-6}$ M retinoic acid (HL-60 only).

Nuclear run-on assays were performed as previously described (Satterthwaite A. B. et al., *Blood* 75:2299 (1990)). The following DNAs were used to prepare slot blots: the plasmid CDM8 (Seed B., *Nature* 329:840 (1987)); a 4.1 kb XbaI fragment of CD11b cDNA containing the complete coding region in the vector CDM8 (Arnaout M. A., et al., *J. Cell Biol.* 106:2153 (1988)); a 3.1 kb SphI/XbaI fragment containing the full length CD18 cDNA in pUC18 (Law S. K. et al., *EMBO. J* 6:915 (1987)); a 1.6 kb EcoRI/ClaI fragment of the human c-myc exon 3 in pSP65 (Dalla Favera R. et al., *Proc, Natl. Acad. Sci. USA* 79:6497 (1982)); a 2 kb PstI fragment of the chicken actin cDNA in pBR322 (Cleveland D. W. et al., *Cell* 20:95 (1980)); a 1.5 kb XbaI fragment containing the cDNA encoding CD33 in the vector CDM8 (Simmons D. and Seed B., *J. Immunol.* 141:2797 (1988)), and a 1.3 kb EcoRI fragment the 3' end of the myeloperoxidase cDNA in the vector bluescript. (Weil S. C. et al., *Proc. Natl, Acad. Sci. USA* 84:2057 (1987)). Autoradiograms were exposed at –80° C. with an intensifying screen and quantitated on a densitometer whereby background hybridization to the plasmid CDM8 was subtracted from all other values.

Data from this assay demonstrate that CD11b transcription rate increases approximately 8-fold in U937 cells and 14-fold in HL-60 cells after differentiation with TPA, and that induction of HL-60 with retinoic acid results in a 5-fold increase in transcription. These increases are similar in magnitude to the increases in the steady state levels of CD11b mRNA seen following induction, demonstrating that CD11b mRNA expression is largely controlled at the level of transcription. Increased rates of CD18 transcription and decreased rates of myc and MPO transcription following differentiation have previously been reported and were used as controls (Hickstein D. D. et al., *J. Bio. Chem.* 263:13863 (1988); Bentley D. L. and Groudine M., *Nature* 321:702 (1986); Tobler A. et al., *J. Cell. Physiol.* 136:215 (1988)).

Characterization of the CD11b Promoter in Transient Transfections

A 1.7 kb fragment of CD11b 5' flanking DNA extending to bp +83 of the cDNA (just proximal to the translational start site ATG at bp +84) was cloned upstream of and operationally linked to a luciferase reporter gene. This construct directed reporter gene activity 600 fold above background (promoterless luciferase vector, FIG. 15) when transfected into U937 cells which were induced to differentiate with $3 \times 10^{-8}$ M TPA immediately following transfection; we observed activity 144 fold above background in uninduced U937 cells.

The –1704 bp promoter also directed luciferase activity 25 fold above background in uninduced HL-60 cells (HL-60 cells are 100 fold less transfectable than U937 cells). Luciferase activity in these cells increased to 480 fold above background when the cells were induced with TPA. (Pahl H. L. et al., *Exp. Heme.* 19:1038 (1991)). We confirmed by 5' RACE (Frohmann M. A. et al., *Proc. Natl. Acad. Sci. USA* 85:8998 (1988)) that initiation of reporter gene transcription occurred at the predicted CD11b start site.

The promoter for the proto-oncogene c-myc, whose transcription rate is down regulated upon induction of myeloid cells with TPA (Bentley D. L. and Groudine M., *Nature* 321:702 (1986)), directed the expression of luciferase activity. This activity decreased two fold upon induction with TPA, indicating that the TPA induced up-regulation of CD11b promoter activity represents a cell or developmental stage specific effect. A 3.2 kb fragment containing the transcriptional start site and 2 kb of 5' flanking DNA of the myeloperoxi-dase gene failed to direct any measurable reporter gene activity in either U937 or HL-60 cells. These results demonstrate the need for a functional promoter to direct reporter gene activity in this assay.

Seven deletion mutants of the –1704 bp CD11b promoter were generated. 20 µg of each deletion mutant were transiently transfected into U937 cells which were then immediately induced with $3 \times 10^{-8}$ M TPA. Transfections were performed as described in Example 1, with one alteration: $3 \times 10^{-7}$ cells were used per electroporation. Results were normalized for transfection efficiency to the amount of growth hormone expressed from 2 µg of cotransfected plasmid (CMV early promoter driving growth hormone transcription). Growth hormone levels correlated with the amount of transfected plasmid as detected by quantitative slot blot hybridization of DNA isolated from transfected cells by Hirt extraction (Hirt B., *J. Mol, Biol,* 26:365 (1967)).

Figure 6:
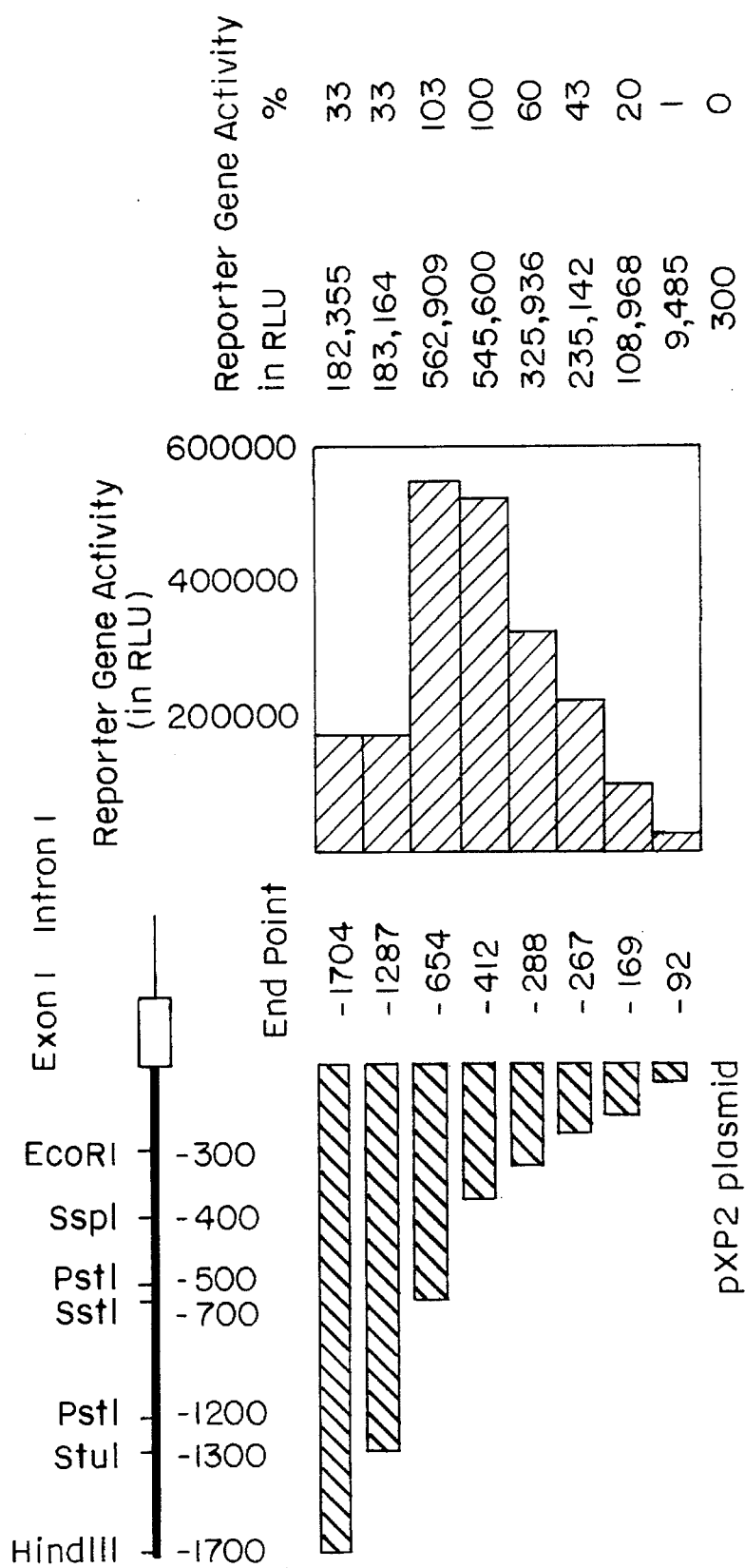
FIG. 6 depicts deletion analysis of the CD11b promoter.

Luciferase activity was determined 14 hours post transfection and is reported, in FIG. 6, in relative light units (RLU). Values given are corrected for transfection efficiency, and representative values of duplicate experiments are shown. Results shown in FIG. 6 indicate that a construct extending from bp –412 to bp +83 is three times more active in U937 cells than a construct extending from bp –1704 to bp +83. However, deletions of the promoter ending 3' of bp –412 show diminished activity, suggesting the presence of positive regulatory elements in this region.

The construct retaining only the first 92 bp of CD11b 5' flanking DNA, although 100 fold less active than the 412 bp construct, still directs high levels of reporter gene activity (30 fold above background), demonstrating the presence of strong promoter elements immediately adjacent to the transcriptional start site.

Transfection into uninduced U937 cells yields similar relative results; however, for all deletion mutants tested, the levels of reporter gene activity were increased five fold with TPA induction.

Deletion and Point Mutants of the CD11b Promoter

The –1704 bp CD11b promoter/luciferase construct was generated by cloning a HindIII/SmaI fragment from CD11b genomic lambda phage 65-3 (Coffin J. E. et al., *Blood* 78:108a (1991)) into the luciferase vector pXP2 (Nordeen S. K., *BioTechniques* 6:454 (1988)). This fragment extends from bp –1704 to +83 in the genomic sequence, whereby bp +1 denotes the transcriptional start site.

Deletion mutants at bp –1287, bp –654, and bp –412 were generated using restriction endonucleases StuI, SstI and SspI respectively (Coffin J. E. et al., *Blood* 78:108a (1991)). Deletions ending 3' of bp –412 were generated using Exonuclease III digestions. (Henikoff S., *Gene* 28:351 (1984)). The GATA site at bp –41 to bp –38 was mutated by oligonucleotide directed PCR mutagenesis (Kadowaki H. et al., *Gene* 76:161 (1989)) to the sequence GTTA.

For DNA binding studies, a 122 bp fragment, extending from bp –90 to bp +32, either containing the wild type GATA sequence or the mutant GTTA was used; for transfections the GTTA mutation was placed in the context of the 1.7 kb CD11b promoter fragment. All deletion end points and mutants were determined and confirmed by sequence analysis (Sanger F. et al., *Proc. Natl. Acad. Sci. USA* 74:5463 (1977)).

Nucleotide Sequence of the CD11b Promoter

The first 412 bp of the CD11b promoter were sequenced on both strands, with the result shown in FIG. 1. The CD11b promoter contains two consensus binding sites for Sp1 at bp −64 and −103 and a purine rich potential PU.1 site (Karim F. D. et al. *Genes Dev.* 4:1451 (1990); Galson D. L. and Housman D. E., *Mol. Cell Biol.* 8:381 (1988)) at bp −134. The CD11b promoter, like other myeloid promoters, such as CD13, (Shapiro L. H. et al., *J. Bio. Chem.* 266: 11999 (1991)), and CD18, contains neither a TATAA box nor a CCATT box.

In FIG. 1, the transcriptional start site is indicated as bp +1 (Coffin J. E. et al., *Blood* 78:108a, (1991)). The Sp1 sites at bp −64 and bp −103, the GATA site at bp −42, and the PU.1 site at bp −134 are underlined. The myeloid consensus sequence (Shapiro L. H. et al., *J. Bio, Chem,* 266:11999 (1991)) is overlined. The predicted amino acid sequence, beginning with the methionine at bp +84 is indicated below the bottom line of sequence in upper case italicized single letter code, and the first intron, beginning at bp +112, is indicated in lower case letters. This sequence has been deposited in the Genbank data base (accession no. M80772).

The transcriptional start site for CD11b (Coffin J. E. et al., *Blood* 78:108a (1991)) does not fit a consensus cap site sequence (Corden J. et al., *Science* 209:1405 (1980)), nor is there an "initiator" sequence, as described in the TATA-less promoter for terminal transferase (Smale S. T. and Baltimore D., *Cell* 57:103 (1989)). Although the CD11b promoter is responsive to TPA, there are no consensus binding sites for AP-1 (Lee W. et al., *Cell* 49:741 (1987)) or NF-kB (Sen R. and Baltimore D., *Cell* 46:705 (1986)), transcription factors known to mediate TPA inducibility in other promoters.

The GATA Site is Non-Functional in U937 Cells

The consensus sequence GATA is found at bp −41 to −38 of the CD11b promoter. A GATA site at bp −50 in the integrin platelet factor IIb promoter is necessary for efficient transcription of this gene (Romeo P. H. et al., *Nature* 344:447 (1990)). Therefore, a point mutant was used to test whether the GATA site in the CD11b promoter is functional.

A point mutation in the 1.7 kb CD11b promoter fragment changing the sequence GATA to GTTA did not reduce the level of reporter gene activity obtained in transient transfection of U937 cells. An electrophoretic mobility shift assay (Fried M. and Crothers D. M., *Nucl. Acid. Res.* 9:6505 (1981)) was used to determine that GATA protein binds the wild type CD11b promoter and that binding was obliterated by the point mutation.

Tissue Specificity Of the CD11b Promoter in vitro

In order to determine the tissue specificity of the CD11b −1.7 kb flanking region, several constructs were transfected into HeLa cells, which do not express CD11b. The −412 bp promoter directs $7.5 \times 10^5$ relative light units (RLU) in U937 cells and $7.7 \times 10^3$ RLU in HeLa cells, and the −92 bp promoter directs $9.2 \times 10^4$ RLU in U937 and 849 RLU in Hela (values corrected for transfection efficiency). Therefore, both the −412 bp and the −92 bp construct yield 100 fold less activity in HeLa cells than in U937, and the tissue specificity of the CD11b promoter is retained even in the first 92 bp of the 5' flanking region.

Example 3 - A Myeloid Factor Binds the CD11b Promoter

In order to characterize transcription factors that regulate CD11b promoter activity, an electrophoretic mobility shift assay (EMSA) was used to locate proteins interacting specifically with the CD11b promoter. 10 µg of nuclear extracts from TPA induced U937 cells or HeLa cells were used in an EMSA. Oligonucleotides representing bp −26 to bp +2 of the wild type CD11b promoter, the mutant m1 (Table II), and a 30 bp oligonucleotide from bp −144 to bp −115 of the wild type CD11b were used as probes. These and additional oligonucleotides used in these Examples are listed in Table II, which gives the names, abbreviations and sequences of oligos used in EMSAs. Mutated nucleotides in oligonucleotides m1, m2 and m3 are indicated with an asterisk (*) above the base, and the core binding region for ets family transcription factors is underlined. The CD11b sequences in the −26– +2 region are presented as the antisense strand so as to facilitate comparison with the CD11b −130 site as well as the mouse β-globin IVS2 site. Unlabeled competitor oligos were added at 50 fold molar excess over probe oligos. In order to achieve adequate separation of bands A and A*, the gel was electrophoresed sufficiently long so that unbound (free) probe was run off the bottom. Similar results were obtained with gel runs of shorter duration, in which the free probe remained on the gel.

TABLE II

| Oligonucleotides Used in EMSAs | | |
|---|---|---|
| Name | Abbreviation | Sequence |
| CD11b wild type −26 to +2 | (wt-26) | +2 GCTCAAAGAAGGGCAGAAAAGGAGAAGTAGG (SEQ ID NO: 13) |
| CD11b mutant 1 −26 to +2 | (m1) | +2 GCTCAAAGAAGGGCAGCCCGGGAGAAGTAGG (SEQ ID NO: 14) |
| CD11b mutant 2 −26 to +2 | (m2) | +2 GCTCAAAGAAGGGCAGAAAAGTCGACGTAGG (SEQ ID NO: 15) |
| CD11b mutant 3 −26 to +2 | (m3) | +2 GCTCAAAGAAGGGCAGAAAAGCTGCAGTAGG (SEQ ID NO: 16) |
| CD11b wild type −144 to −115 | (wt-144) | −144 GGAAGCTGGGGAGGAAGGGTGGGCAGGCTG - 115 (SEQ ID NO: 17) |
| globin wild type PU.1 site | (wt IVS) | ACCTRCCTATCAGAAAAAAGGGGAAGCGA (SEQ ID NO: 18) |

TABLE II-continued

Oligonucleotides Used in EMSAs

| Name | Abbreviation | Sequence |
| --- | --- | --- |
| globin mutant PU.1 site | (x IVS) | ACCTRCCTATCAGAAAAACCCGGGAAGCGA (SEQ ID NO: 19) |

The probes were labeled with [gamma-$^{32}$P] ATP (NEN) to a specific activity of $2\times10^8$ cpm/μg as previously described (Maxam, A. M. and Gilbert, W. *Meth. Enzymol.* 65:499–560 (1980)). An additional AG or GCT were included at the 5' or 3' end of the oligonucleotides, respectively, to create restriction endonuclease compatible overhands. 0.5 ng of probe was incubated with 10 μg of nuclear extract in 20 μl containing a final concentration of 10 mM Hepes pH 7.5, 50 mM KCl 0.5 mM MgCl 2, 1mM DTT, 1mM EDTA and 5% glycerol on ice for 15 minutes. Unlabeled competitor oligonucleotides were added to the nuclear extracts immediately prior to the addition of the radioactive probe. Reactions were electrophoresed at 14 V/cm on a 6% polyacrylamide gel cast in 0.5×TBE (45 mM Tris-borate, 45 mM boric acid, 1 mM EDTA) at 4° C. In order to achieve adequate separation, the gel was electrophoresed sufficiently long so that unbound (free) probe was run off the bottom. Similar results were obtained with gel runs of shorter duration, in which the free probe remained on the gel. RNA produced by in vitro transcription of a plasmid containing the 1.5 kb mouse PU.1 cDNA was run on one lane of the gel.

The RNA was translated in vitro using a rabbit reticulocyte lysate system (Promega) as previously described (Glass, C. K. et al., *Nature* 329:738–741 (1987)). [$^{35}$S] methionine-labeled protein was analyzed by SDS-polyacrylamide gel electrophoresis and used to normalize the amount of unlabeled protein (translated in parallel) used in the gel retardation assays. A single major translated product, corresponding to a relative molecular weight of 32 kDa, was observed. In another lane, 1 μl of a polyclonal rabbit antisera raised against PU.1, or 1 μl of preimmune serum, was added to the nuclear extract and preincubated on ice for 15 minutes. The radiolabeled probe was then added and the reaction incubated on ice for an additional 15 minutes. The serum was raised against a 13 amino acid peptide of PU.1 (amino acid 33 to 45 of the mouse PU.1 protein (Klemsz, M. J. et al., *Cell* 61:113–124 (1990)), corresponding to amino acid 33 to 45 of the human PU.1 protein (Ray, D. et al., *Oncogene* 5:663–668 (1990)). This peptide is 85% conserved across the two species.

Results of these experiments show that a protein in the myeloid cell line U937, but not in cervical carcinoma HeLa cells, specifically bound the CD11b promoter between by −26 and bp +2. Binding was competed by the addition of excess unlabeled probe, but not by a probe containing a 4 bp mutation at bp −12 to −15 (mutant m1). In addition, the mutant probe did not bind the protein, indicating that bp −12 to −15 of the CD11b promoter are critical for interaction with this protein. An oligonucleotide from bp −144 to −115 of the CD11b promoter, containing a very similar sequence, likewise neither competed for nor bound this protein. The sequence AAAAGGAGAAG (SEQ ID NO: 2) resembles within the CD11b promoter region the consensus binding sequence for members of the ets family of transcription factors (Klemsz, M. J. et al., *Cell* 61:113– 124 (1990)). The proto-oncogene PU.1, a member of the ets family, is specifically expressed in B cells and macrophages (Klemsz, M. J. et al., *Cell* 61:113–124 (1990)). An oligonucleotide containing a characterized PU.1 biding site from the β-globin gene (Galson, D. L. and Housman, D. E., *Mol. Cell. Biol.* 8:381–392 (1988)) competes for binding to the CD11b promoter. However, an oligonucleotide containing a 3 bp mutation in the β-globin PU.1 site, analogous to the mutation created in the CD11b promoter, did not compete for binding to the CD11b promoter. Competition by a known PU.1 site indicates that the PU.1 transcription factor is the protein binding to the CD11b promoter.

Mutations in the PU.1 site at bp −20 of the CD11b promoter were generated using oligonucleotides carrying point mutations (Zaret, K. S. et al., *Proc. Natl. Acad. Sci.* 87:5469–5473 (1990)). Three different mutations were generated for use in this and the following Examples. CD11b m1 mutation changed the sequence AAAA at bp −12 to −15 on the noncoding strand to CCCG, while CD11b m2 mutation and CD11b m3 mutation changed the sequence GAGAA at bp −17 to −21 on the noncoding strand to TCGAC and CTGCA, respectively (See Table II). Mutant CD11b promoter fragments were generated by PCR and cloned into the vector pXP2 (Nordeen, S. K., *BioTechniques* 6:454–457 (1988)). The sequence of the mutant constructs was confirmed by the dideoxy chain termination method (Sanger, F. et al., *Proc. Natl. Acad. Sci., USA* 74:5463–5467 (1977)).

Example 4 - Tissue Distribution of the CD11b Promoter Binding Activity

The tissue distribution of the CD11b promoter binding activity was investigated by an EMSA using nuclear extracts from several different cell lines and the CD11b −26 to +2 bp probe. 10 μg of nuclear extracts from TPA induced U937 cells, Haftl B cells, Jurkat T cells or glioma cells were added to an EMSA using bp −26 to bp +2 of the wild type CD11b promoter as a probe. Unlabeled competitor oligos were added at 50 fold excess over probe oligo. The conditions for the EMSA were as described above.

The human promonocytic cell line U937 (ATCC # CRL 1593) was grown to $2\times10^5$ cells/ml and induced with $3\times 10^{-8}$ M TPA (Sigma, St. Louis, Mo.) for 24 hours prior to harvest for nuclear extraction. The human epithelial carcinoma cell line HeLa (ATCC # CCL 2) was harvested in early logarithmic growth phase. Nuclear extracts were prepared as previously described (Pahl, H. L. et al., *Exp. Hematol*, 19:1038–1041 (1991)) with one modification: the following protease inhibitors were added at the final concentration indicated to every buffer immediately prior to use: 1 mM phenylmethylsulfonyl fluoride (PMSF), 1 μg/ml Pepstain A, 0.5 μg/ml Chymostatin, 1 μg/ml Antipain, 1 μg/ml Leupeptin, 4 μl/ml Aprotinin (all from Sigma). Protein concentrations were determined using the Bradford assay (BioRad, Richmond, Calif.) and bovine serum albumin standards (Sigma).

The results of the EMSA demonstrate that a myeloid factor binds to bp −26 to +2 of the CD11b promoter region. In addition, these data indicate that specific binding to the CD11b promoter oligonucleotide occurs only when extracts from TPA-induced U937 cells (macrophage) or Haft1 (B cell) were used, and not in extracts from Jurkat (T cell), U2-SIMG (glioma) or HeLa cells. Thus, the tissue distribution of the CD11b promoter binding activity resembles that of PU.1.

Example 5 - The proto-Oncogene PU.1 Binds the CD11b Promoter

To provide further evidence that the CD11b promoter binding activity was caused by PU.1, the electrophoretic mobility of the complex specifically bound to CD11b wild type bp −26 to +2 probe (complex A and A*) was compared with that formed by in vitro translated PU.1 protein in the presence of probe. The probe used in this assay was the CD11b wild type −26 to +2 oligo (Table II). In this assay, complex A comigrated with a specific complex observed when in vitro translated PU.1 is incubated with the CD11b wild type −26 to +2 probe. For final confirmation that PU.1 binds the CD11b promoter, an assay was performed using an antibody that reacts specifically with the amino terminal end of PU.1 and produces a "supershift" of bound protein when added to an EMSA. Addition of anti-PU.1 peptide antibody, but not of preimmune serum, resulted in a supershift of protein bound to the CD11b promoter, thereby identifying it as PU.1. A second, lower band (A*) did not supershift. This lower band was only seen in extracts from U937 cells, and not B cells, and may be the result of proteolysis which we have previously observed during nuclear extract preparation from myeloid cells (Galson, D. L. and Housman, D. E., *Mol. Cell. Biol.* 8:381–392 (1988)). If the relevant epitope is lost, the anti-PU.1 antibody may not recognize a proteolytically cleaved PU.1. Alternatively, the lower band (A*) may represent a second, distinct protein with binding activity to the CD11b promoter.

Example 6 - The PU.1 Binding Site at bp −20 is Protected from DNase I Digestion in Myeloid Cells in vitro DNase I footprinting assays were performed on the CD11b promoter with nuclear extracts in order to fully characterize the PU.1 binding site. The coding strand of the CD11b promoter was labeled and subjected to chemical sequencing, DNase I digestion, or incubated with 80 µg of U937 nuclear extract (uninduced or induced with TPA), or 80 µg of HeLa cell nuclear extract, and subsequently subjected to DNase I digestion. The pattern observed after DNase I digestion of plasmid DNA remained unchanged after the addition of HeLa nuclear extract. However, after addition of U937 nuclear extract, bp −9 to bp −26 on the coding strand and bp −10 to bp −29 on the non-coding strand are protected from DNase I digestion. In addition, bp −8 and −43 became hypersensitive to DNase I digestion. This footprint was competed by the addition of 50 fold molar excess of non-radioactive β-globin PU.1 binding site oligonucleotide. Therefore, PU.1 is the only DNA binding activity detectable in this region. TPA induction of U937 cells does not alter PU.1 binding. Similarly, Northern blotting and EMSA revealed no change in either PU.1 mRNA or DNA binding activity following TPA induction. Thus, DNaseI footprinting analysis places the PU.1 binding site between bp −9 and bp −29 of the CD11b promoter, and is consistent with the results obtained from EMSA.

For in vitro footprinting analysis, a 370 bp fragment extending from the EcoRI site at bp −264 of the CD11b promoter to the HpaI site at bp +106 (Larrick, J. W. et al., *Immunol*, 125(1):6–12 (1980)) was subcloned into pGEM 2zf(+) (Promega, Madison, Wis.). The resulting plasmid was then digested with EcoRI and HindIII to release the insert, which was radioactively labeled at the HindIII site (coding strand) or the EcoRI site (non-coding strand) using [alpha-$^{32}$P] dATP as previously described (Ray, D. et al., *Oncogene* 5:663–668 (1990)). 80 µg of HeLa or U937 cell nuclear extracts were incubated with 10 ng of DNA probe, labeled to a specific activity of $1.5 \times 10^6$ cpm/µg, and 4 µg of poly didC (Promega) in 10 mM HEPES (pH 7.8), 30 mM KCl, 12% glycerol, 5 mM $MgCl_2$, 0.5 mM dithiothreitol, 0.1 mM EDTA and 0.2 mM PMSF on ice for 30 minutes. The DNA was cleaved with 180 ng of DNase I at room temperature for 1 minute. Reactions were terminated by the addition of 100 µl of stop solution (20 mM EDTA, 0.5% SDS, 20 mM Tris (pH 7.5), 75 µg/ml sheared salmon sperm DNA, 100 µg/ml proteinase K) and subsequent incubation at 37° C. for 30 minutes. Reactions were extracted with an equal volume of phenol:chloroform, ethanol precipitated, and products analyzed on a 6% denaturing polyacrylamide gel. Chemical sequencing reactions (Ray, D. et al., *Oncogene* 5:663–668 (1990)) of the same DNA were used as size standards.

Example 7 - The PU.1 Binding Site is Essential for High Level CD11b Promoter Function A mutation in the PU.1 site was constructed, and the ability of the wild type and mutant CD11b promoter to direct reporter gene activity in transient transfection assays was compared. U937 and HeLa cells were transfected by electroporation in Iscove's Modified Eagle Medium at 960 µF and 250 V or 150 V, respectively, as previously described (Pahl, H. L. et al., *Blood* 79:865–870 (1992)). Cells were induced with $3 \times 10^{-8}$ M TPA (Sigma, St. Louis, Mo.) immediately following transfection, and luciferase activity was determined 14 hours post transfection. The results of this comparison are shown in FIG. 7. Luciferase assays were performed as previously described, and data presented in relative light units (RLU). Transfection efficiency was normalized to the levels of growth hormone expressed from 2 µg of cotransfected plasmid containing the cytomegalovirus (CMV) promoter directing growth hormone expression (Pahl, H. L. et al., *Blood* 79:865–870 (1992)). Growth hormone concentrations were measured by radioimmune assay (RIA) (Nicol's Institute, San Juan Capistrano, Calif.).

A mutation of the PU.1 site which abolished both competition for and binding to the PU.1 protein was introduced both in the context of the 412 and the 92 bp promoter (mutation m1, Table II) (Pahl, H. L. et al., *Blood* 79:865–870 (1992)). Introduction of this mutation resulted in a 3–4 fold decrease in reporter gene activity compared to the wild type promoter following transient transfections into the myeloid cell line U937. In contrast, transfections into HeLa cells, which do not express PU.1, showed no decrease in reporter gene activity following mutation of the PU.1 site.

Example 8 - Characterization of the Non-Consensus PU.1 Core Binding Site

Because the PU.1 binding site in the CD11b promoter does not contain the core consensus sequence 5' GGAA 3' (Karim, F. D. et al., *Genes Dev.* 4:1451–1453 (1990)), and because a sequence at bp −130 of the CD11b promoter containing this consensus does not bind PU.1, the importance of the core region for PU.1 binding was investigated. Two point mutations (m2 and m3) were constructed as described in Example 3 above, and tested by EMSA for the ability to bind the CD11b promoter in nuclear extracts from U937 cells. Both of these mutations disrupt the sequence 5' GGAGAA 3' between bp −16 and −21 of the CD11b promoter. 10 μg of nuclear extracts from TPA induced U937 cells were used in the EMSA. Probes included bp −26 to bp +2 of the wild type CD11b promoter, the mutant m2 probe, and the mutant m3 probe. Unlabeled competitor oligos were added at 50 fold excess over probe oligo.

Figure 8:
FIG. 8 is a summary of in the binding to the CD11b promoter showing the sequence of the promoter between bp −35 and bp −5 (SEQ ID NO: 20).

Mutants m2 and m3 neither compete for nor themselves bind PU.1. FIG. 8 summarizes the mutations demonstrated to interfere with DNA binding by PU.1. The data presented are from EMSA and in vitro footprinting assays performed as described above. In this figure, dashes (-) between base pairs denote bases implicated in PU.1 binding by EMSA; brackets span sequences protected from DNaseI digestion during in vitro footprinting assays.

Characterization of Regulatory Sequences Important for CD11b Promoter Activity

Recently, PU.1, a member of the ets family of transcription factors, was shown to be expressed principally in B cells and macrophages (Klemsz, M. J. et al., Cell 61:113–124 (1990)). PU.1 is identical to the Spi-1 proto-oncogene, which was isolated as the site of Friend erythroleukemia virus integration in 95% of friend virus induced tumors in mice. Viral insertion into this region of the mouse genome results in transcriptional activation and enhanced expression of PU.1/Spi-1 mRNA (Goebl, M. G. et al., Cell 61:1165–1166 (1990); Moreau-Gachelin, F. et al., Nature 331:277–280 (1988)). DNA binding studies have identified the consensus sequence for PU.1 binding as purine rich segments containing a 5'-GGAA -3' core sequence (Karim, F. D. et al., Genes Dev. 4:1451– 1453 (1990)). Although PU.1 binding to B cell and erythroid enhancers has been demonstrated, the effect of PU.1 binding site mutations on the function of complete promoters/enhancers has not been investigated (Galson, D. L. et al., Mol. Cell. Biol. 8:381–392 (1988); Pongubala, J. M. R. et al., Mol. Cell. Biol. 2:368–378 (1992)). Moreover, no macrophage targets for this transcription factor are known.

Results herein presented demonstrate that a sequence at approximately bp −20 of the myeloid specific CD11b promoter binds PU.1, and that a mutation of this site, which results in the loss of PU.1 binding activity, reduces the ability of the CD11b promoter to function in myeloid cells (U937) but not in cervical carcinoma cells (HeLa). Thus, tissue specific expression of the 92 bp CD11b promoter is regulated to a large extent by the PU.1 site. Mutation of the PU.1 site reduces the ratio of reporter gene activity between myeloid cells and cervical carcinoma cells from 15:1 to 2.5:1. However, because PU.1 is expressed in both B cells and myeloid cells, and CD11b expression is restricted to myeloid cells, PU.1 cannot represent the sole determinant of tissue specificity of the CD11b gene. These results indicate that additional transcription factors interact with PU.1 to modulate its activation of tissue specific transcription.

Mutation of the PU.1 site in the CD11b promoter significantly reduced promoter activity, but did not entirely abolish promoter activity. The m1 mutation (Table II) was used to determine whether PU.1 interacts with transcription factors which bind the CD11b promoter between bp −92 and bp −412. Mutation m1, in both the context of the 92 bp and the 412 bp promoter, reduced activity of the CD11b promoter 3–4 fold indicating that PU.1 does not interact with transcription factors that bind the CD11b promoter between bp −92 and bp −412. PU.1 may nonetheless act synergistically with proteins which bind within the 92 bp promoter. Sequence analysis shows several additional putative transcription factor binding sites within the first 92 bp: an SP1 box at bp −64 and a GATA motif at bp −42. Mutations of the SP1 site significantly reduce CD11b promoter activity in U937 cells and, in contrast to the m1 mutant, in HeLa cells as well.

Electrophoretic mobility shift assays (EMSA) using nuclear extracts from U937 cells consistently show two complexes (A and A*) binding the CD11b promoter. A* may represent a proteolytic cleavage product of band A. Alternatively, the two bands may represent distinct proteins. Although these two possibilities have not yet been conclusively distinguished, several observations indicate that A* represents a proteolytic cleavage product of A, and is therefore likely to be a cleaved PU.1 protein. Firstly, both complexes bind specifically to both the CD11b promoter at −20 and to the mouse beta globin IVS2 PU.1 site, and do not bind to the CD11b upstream sequence GAGGAA at bp −144. Both complexes react identically with respect to mutations; i.e., mutations m1, m2 and m3 in the CD11b promoter and a mutation in the beta globin IVS2 do not compete for binding of either complex to the wild type promoter, nor do they bind either complex A or A*. Secondly, myeloid cells such as U937 contain high levels of protease activity and, therefore, isolating nuclear extracts without any proteolytic cleavage is extremely difficult (Galson, D. L. and Housman, D. E. Mol. Cell. Biol. 8:381–392 (1988)). Moreover, the PU.1 protein is exquisitely sensitive to proteolysis because it contains a PEST region, an amino acid segment rich in proline (P), glutamic acid (E), serine (S) and threonine (T), implicated in targeting proteins for degradation (Klemsz, M. J. et al., Cell 61:113–124 (1990)). We have observed two complexes similar to A and A* in macrophage lines (HL-60 and WEHI-3) and not in B cell lines, and have demonstrated that the two complexes involved the same DNA binding site (Galson, D. L. and Housman, D. E. Mol. Cell. Biol. 8:381–392 (1988)). Likewise, nuclear extracts from Haft1 (B cell) cells form only one protein/DNA complex with the CD11b promoter. PU.1 may be protected from cleavage in B cells by interaction with an additional protein which masks the PEST region (Pongubala, J. M. R. et al., Mol. Cell. Biol. 12:368–378 (1992)). Alternatively, B cells may contain fewer proteases and yield proteolytically intact extracts.

The data herein presented demonstrate that complex A and A* have indistinguishable DNA binding activities. Full length PU.1 produced using in vitro translation forms a complex indistinguishable from complex A in gel shift experiments. The in vitro translated complex can be supershifted with the anti-PU.1 amino terminal peptide antibody (and not with control antibody) in a manner indistinguishable from complex A isolated from macrophage cell lines. Therefore, complex A most likely represents full-length PU.1 protein. Klemsz, M. J. et al. Cell 61:113–124 (1990) demonstrated that the carboxyl terminal portion of the PU.1 molecule contains the DNA binding activity. The antibody used in the supershift experiment is raised against the amino terminal region (amino acids 33 to 45). These data indicate that the larger complex A reacts with the amino terminal antibody, while the smaller A* does not. If PU.1 is cleaved at the PEST site in macrophage cells, and complex A represents a complex formed by uncleaved PU.1, then one would predict that complex A* would not react with the antibody but would bind DNA in a manner indistinguishable from complex A, which is precisely what we observed.

Although unlikely, it is yet possible that complex A* represents a protein distinct from PU.1. Although the anti-PU.1 antibody used does not recognize any other known ets family protein (Pongubala, J. M. R. el al., *Mol. Cell. Biol.* 12:368–378 (1992)), the possibility that the protein binding the CD11b promoter is distinct from but highly similar to PU.1 cannot be excluded.

The PU.1 binding site at bp −20 (AAAAGGAGAAG) (SEQ ID NO: 2) does not conform to the previously described consensus binding site for PU.1 and other ets family proteins (GGAA) (Karim, F. D. et al., *Genes Dev.* 4:1451– 1453 (1990)), whereas a purine rich sequence at bp −140 of the CD11b promoter, which contains the consensus sequence (GGGGAGGAAGGG (SEQ ID NO: 3; see also Table II), neither bound PU.1 nor competed for PU.1 bound at bp −20. The presence of the GGAA core is therefore not sufficient for PU.1 binding. Mutations of the non-consensus core region of the CD11b PU.1 binding site (mutations m2 and m3) disrupt PU.1 binding. In addition, the m1 mutation, which no longer binds PU.1, does not disrupt the core, but disrupts the adjacent 5' purine rich stretch of DNA. These data support the conclusion that the bases outside the PU.1 core consensus region influence PU.1 binding, as previously described (Galson, D. L. and Housman, D. E. *Mol. Cell. Biol.* 8:381–392 (1988); Wasylyk, C. et al., *Genes and Dev.* 6:965–974 (1992)). These data also indicate that the core site itself contains more sequence variation than the previously defined consensus sequence. Furthermore, as measured by in vitro footprinting assays, bp −8 and −43 become hypersensitive to DNase I digestion following PU.1 binding. This hypersensitivity is not competed by the addition of unlabeled oligonucleotide which abolished PU.1 binding. This hypersensitivity may reflect binding of other factors on either side of the PU.1 site.

The following Example shows that the transcription factor and proto-oncogene product, PU.1 binds at bp −20 of the CD11b promoter, and that mutation of this site significantly reduces CD11b promoter activity.

Example 9 - Linker scanning analysis of the CD11b −92 bp promoter reveals an essential region centered at bp −60

In order to identify additional sequences required or useful for CD11b promoter activity, 9 linker scanning mutations were constructed by inserting a 10 bp oligonucleotide linker consecutively every 10 bp in the promoter (for sequences see FIG. 9). In other words, a 10 bp linker, containing a BamHI restriction site (sequence 5' GGATCCCAGA 3') (SEQ ID NO: 4) was substituted for the wild type sequence between bp −95 and −85 (−95/− 85) (SEQ ID No: 25), bp −85 and −75 (−85/−75) (SEQ ID No: 26), bp −75 and −65 (−75/−65) (SEQ ID No: 27), bp −65 and −55 (−65/−55) (SEQ ID No: 28), bp −55 and −45 (−55/−45) (SEQ ID No: 29), bp −45 and −35 (−45/−35) (SEQ ID No: 30), bp −35 and −25 (−35/−25) (SEQ ID No: 31), bp −25 and −15 (−25/−15) (SEQ ID No: 32), and bp −15 and −5 (−15/−5) (SEQ ID No: 33) of the 92 bp CD11b promoter by oligonucleotide directed PCR mutagenesis (Zaret, K. S. et al., *Proc. Natl. Acad. Sci.* 87:5469–5473 (1990). These constructs were tested by transient transfection into U937 cells. The percent change from wild type sequence observed in transient transfection assays with each mutant is shown in the right column of FIG. 8. FIG. 9 depicts the results of the linker scanning analysis. Lines represent wild type sequences and the linker oligonucleotide is represented by a square. Four independent experiments were performed and the average activities and standard errors relative to the 92 bp wild type promoter (100% activity) were calculated. The average luciferase activity is reported in relative light units (RLU) and results are normalized for transfection efficiency. Background luciferase activity, obtained from transfection of the promoterless pXP2 parent plasmid, was 320 RLU.

The linker scanning mutant −15/−5 (FIG. 10) retains only 54% of the wild type promoter activity, thereby confirming previous results showing that mutation of bp −12 to −15 of the CD11b promoter disrupts a PU.1 binding site and decreases the 92 bp promoter activity 3 fold (Pahl, H. L. et al., *J. Biol. Chem.* in press (1993)). In addition, a significant decrease in CD11b promoter activity was seen when sequences between bp −65 and −55, bp −55 and −45 and bp −45 and −35 were replaced (FIG. 9). Because these constructs carry mutations at adjacent sequences, they may each be partially disrupting a sequence required for promoter activity.

Figure 10:
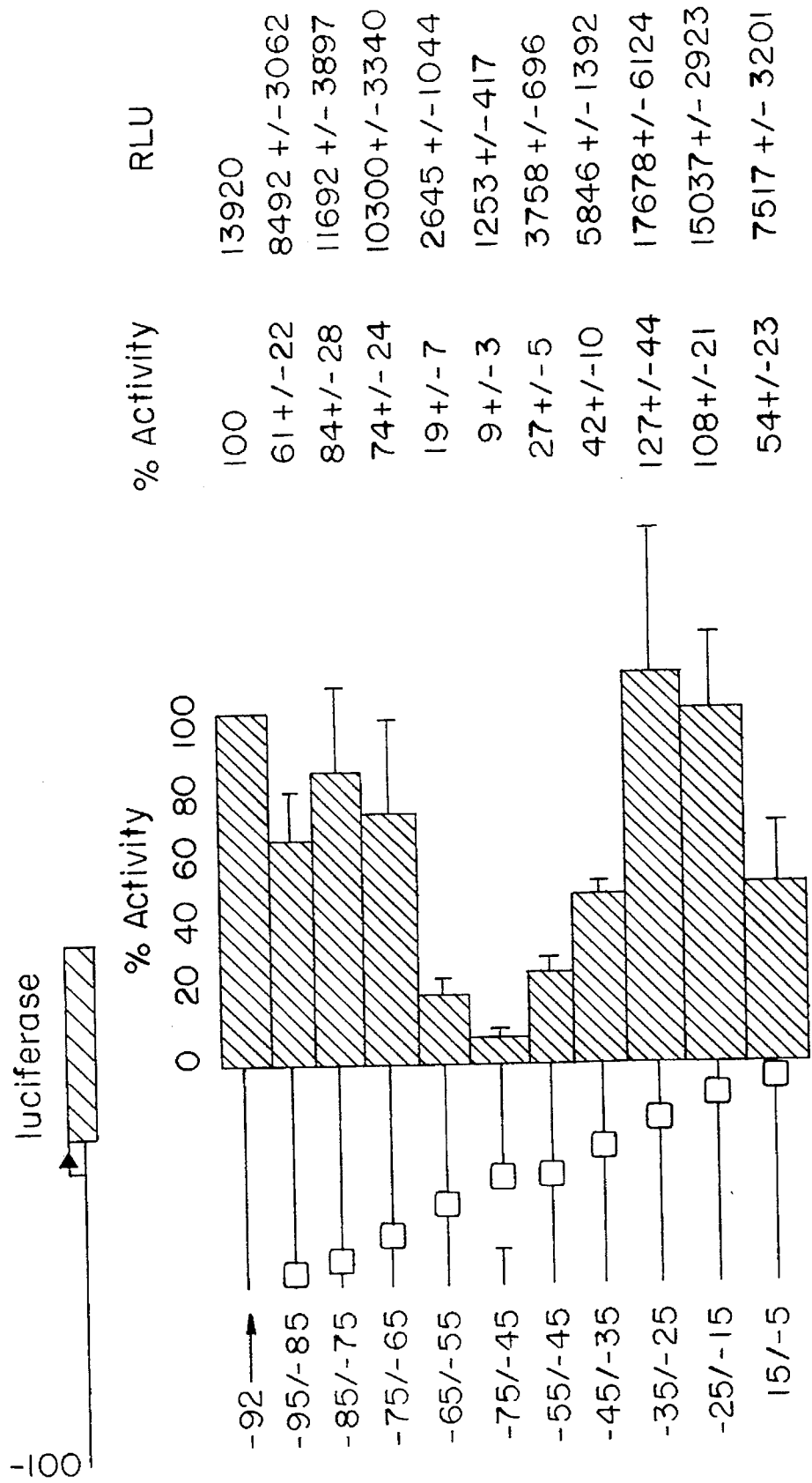
FIG. 10 is a schematic representation of linker scanning analysis of the 92 bp CD11b promoter in transient transfection assays in U937 cells.

Because deletion of the entire region can potentially have a greater effect on CD11b promoter activity than the individual linker scanning mutations, an additional mutant was constructed which substituted bp −75 to bp −45 with the oligonucleotide linker. In the −75/−45 mutant, bp −75 to −45 are replaced by the 10 bp linker oligonucleotide. PCR fragments were cloned into the luciferase vector pXP2 (Nordeen, S. K., *BioTechniques* 6:454–457 (1988)) and resulting constructs sequenced to confirm correct placement of the linker oligonucleotide (Sanger, F. et al., *Proc. Natl. Sci., USA* 74:5463–5467 (1977)). This −75/−45 mutant retains only 9% of the wild type 92 bp CD11b promoter activity (FIG. 10). Therefore, sequences between bp −75 and −35 are essential for CD11b promoter activity.

Example 10 - The transcription factor Sp1 binds the CD11b Promoter at bp −60

An electrophoretic mobility shift assay (EMSA) was used to investigate DNA/protein interactions in the CD11b promoter. Nuclear extracts (prepared as described in Example 4 above) from U937 (myeloid) or HeLa (non-myeloid) cells were incubated with a 130 bp probe which extends from bp −90 to bp +40 of the CD11b promoter.

The 130 bp probe represents a BanI/BbsI fragment which extends from bp −90 to bp +40 of the CD11b promoter. This probe was generated by restriction digestion, dephosphorylation, and 5' end labeling (gamma-$^{32}$P ATP, NEN, Cambridge, Mass.) of the resulting fragments. In addition to the 130 bp probe, 30 bp double stranded oligonucleotides were used as probes. The names abbreviations and sequences of the oligos and DNA fragments used in the following EMSAs are shown in Table III.

Nucleotides altered in the bp −78 to −49 mutant oligonucleotide are marked with asterisks (*) in Table III, and the core binding region for the Sp1 transcription factor is underlined. The CD11b sequences in the −114 to −85 region are presented as the noncoding strand so as to facilitate visual comparison with the CD11b −60 site as well as the tissue plasminogen activator (t-PA) site.

TABLE III

DNA Fragments Used in EMSAs

| Name | Abbreviation | Sequence |
|---|---|---|
| CD11b wild type −78 to −49 | wt-78 | bp −78 TGCTCACTGAGCCTCCGCCCTCTTCCTTTG bp −49 (SEQ ID NO:21) |
| CD11b mutant −78 to −49 | m-78 | bp −78 TGCTCACTGAGCCTCCGAGCTCTTCCTTTG bp −49 (SEQ ID NO:22) |
| CD11b wild type −114 to −84 | wt-114 | bp −85 CCTGCCTGGTCTTCCGCCCAGGACTGCCCA bp −114 (SEQ ID NO:23) |
| tissue plasminogen activator wild type | t-PA | AGAAACCCGCCCACACCTCTGGCCCCACCCCTTCTTCA (SEQ ID NO:24) |

These probes were labeled at the 5' ends using gamma -$^{32}$p ATP (NEN). 0.5 ng of probe at a specific activity of 5×10$^6$ cpm/μg (DNA fragments) or 2×10$^8$ cpm/μg (oligonucleotides) were incubated with 10 μg of nuclear extract in 20 μl containing a final concentration of 10 mM Hepes pH 7.5, 50 mM KCl, 5 mM MgCl2, 1 mM DTT, 1 mM EDTA and 5% glycerol on ice for 15 minutes. Unlabeled competitor DNA fragments or oligonucleotides were added to the nuclear extracts at fifty fold molar excess immediately prior to the addition of the radioactive probe. The competitor DNA was a 97 bp HindIII/PstI fragment from the tissue plasminogen activator (t-PA) promoter, which contains two characterized Sp1 sites (Darrow, A. L. et al., Mol. Cell. Biol. 10:5883–5893 (1990)); for partial sequence see Table III). Either polyclonal rabbit antiserum (2892-E), raised against bacterially expressed human Sp1 (Darrow, A. L. et al., Mol. Cell. Biol. 10:5883–5893 (1990)), a generous gift of Dr. Stephen Jackson, or preimmune serum, was added to the EMSA reaction. Three μl of antiserum or preimmune serum (2892-pI) were added to the reaction immediately prior to the addition of radioactive probe. Reactions were electrophoresed at 14 V/cm on a 6% polyacrylamide gel cast in 0.5×TBE (45 mM Tris-borate, 45 mM boric acid, 1 mM EDTA) at 4° C. In order to achieve adequate separation of bands, gels were run sufficiently long so that unincorporated probe was run off the bottom of the gel. Similar results were obtained with gels electrophoresed for shorter time.

In addition to the complex formed by PU.1 described in Examples 3–9 above, two complexes (marked A and A*) specifically bind the CD11b promoter. PU.1 is identified because the complex is competed by the addition of an oligonucleotide spanning the PU.1 site (bp −26 to +2 of the CD11b promoter), but not by addition of oligonucleotides spanning either bp −78 or −49 or bp −114 to −85. A band migrating immediately above the PU.1 band represents non-specific binding to the probe, as it cannot be competed by excess non-radioactive self competitor. In contrast to the PU.1 complex, which is seen only in U937 cell extracts, complexes A and A* are present in both U937 and HeLa cell extracts. These complexes are competed by the addition of excess non-radioactive 130 bp CD11b promoter probe, as well as by the addition of an oligonucleotide spanning bp −78 to −49 of the promoter. A second oligonucleotide, also spanning bp −78 to −49, but containing a 2 bp mutation at bp −60 and −61, no longer competes the binding of complexes A and A*. In addition, whereas the mutant oligonucleotide, when used as a probe, binds neither band A or A*, the wild type oligonucleotide binds both.

The sequence immediately surrounding bp −60 and −61, and thus implicated in the formation of complexes A and A*, 5' CCGCCC 3' is found also at bp −100 of the CD11b promoter (Table III). Interestingly, an oligonucleotide spanning bp −114 to −85 neither competes for binding of complexes A and A*, nor does it itself bind the complexes. Because the sequence between bp −64 and −59, 5' CCGCCC 3', constitutes a consensus binding site for the transcription factor Sp1 (Dynan, W. S. and Tijan, R., Cell 35:79–87 (1983); Letovsky, J. and Dynan, W. S., Nucl. Acid. Res. 17:2639–2653 (1989)), we investigated whether complex A and a' represent Sp1 binding by competing with a 97 bp DNA fragment of the tissue plasminogen promoter (Darrow, A. L. et al., Mol. Cell. Biol. 10:5883–5893 (1990)) containing two characterized Sp1 binding sites (see Table III). Both complexes A and A*, but not the PU.1 complex, are competed by the addition of DNA containing Sp1 binding sites, indicating that they represent Sp1 binding the CD11b promoter.

To investigate whether complex A consists only of the Sp1 transcription factor or perhaps contains additional DNA binding proteins, a comparison was made of the binding of purified Sp1 and nuclear extracts in an EMSA. When purified Sp1 protein is bound to the CD11b promoter bp -90 to +40 probe, the predominant binding activity comigrates with complex A formed by extracts from U937 and HeLa cells. Faint, slowly migrating bands are observed in some of the gel lanes. Because these complexes are competed by the addition of wild type bp −78 oligonucleotide, they most likely represent multimeric complexes of Sp1 binding the Cd11b promoter. Multimeric binding of Sp1 has been observed on other promoters (Darrow, A. L. et al., Mol. Cell. Biol. 10:5883–5893 (1990)). This result suggests that complex A consists only of the Sp1 protein bound to the CD11b promoter and does not contain additional DNA binding proteins.

In order to confirm that complexes A and A* represent Sp1 binding, EMSAs were performed using an antiserum against Sp1, which was previously shown to induce "supershifts" of Sp1 complexes in an EMSA (Darrow, A. L. et al., Mol. Cell. Biol. 10:5883–5893 (1990)). Addition of anti Sp1 antiserum, but not pre-immune serum results in a "supershift" of band A, confirming that band A represents Sp1 binding the CD11b promoter. Complex A* does not supershift after addition of anti Sp1 antiserum; this complex may represent a proteolytically cleaved form of Sp1, which is not recognized by the antibody, a differentially glycosylated form of Sp1 (Schaufele, F. et al., J. Biol. Chem. 265:17189–17196 (1990), or it may represent a second, distinct protein binding the CD11b promoter.

In order to distinguish these possibilities, methylation interference assays were performed as previously described (Baldwin, A. S. and Sharp, P. A., Mol. Cell. Biol. 2:305–313 (1987)) with minor modifications. 50 ng of an oligonucleotide, extending from bp −78 to −49 of the CD11b promoter (wt-78, Table III), or its complement was 5' end labeled with gamma-$^{32}$P ATP (NEN) to a specific activity of 2×10$^8$ cpm/μg. The labeled oligonucleotide was annealed with 2.5

μg of its complementary oligonucleotide in 20 μl containing 20 mM Tris (pH 7.5), 10 mM MgCl$_2$, 50 mM NaCl, and 1 mM DTT, heated to 45° C. for 5 minutes and then allowed to cool slowly to room temperature over 2 hours and incubated overnight at 4° C. Annealed double stranded oligonucleotide, labeled on one end, was purified on a 15% nondenaturing acrylamide gel, and the top band (annealed probe) isolated by the "crush and soak" method (Maxam, A. M. and Gilbert, W., *Proc. Natl. Acad. Sci. USA* 74:506– 564 (1977)). The annealed probe (10 to 50 ng) was treated with 1 μl dimethyl sulfate for 5 minutes at 20° C. in 200 μl of 50 mM sodium cacodylate, 1 mM EDTA, pH 8.0. 2 ng of probe was incubated with either 5 μg of U937 nuclear extract or 0.5 footprinting units (fpu, Promega) of affinity purified Sp1 protein in a preparative mobility shift assay as described above. DNA protein complexes and free (unbound) probe were isolated by agarose gel electrophoresis of the labeled DNA cut from the polyacrylamide gel onto DEAE membranes. Methylated residues were cleaved with 10% piperidine at 90° C. for 30 minutes, and the methylation pattern analyzed on 15% sequencing gels followed by autoradiography at −80° C. with intensifying screens.

The wild type CD11b promoter oligonucleotide (wt-78, Table III) was end labeled on the coding strand with gamma-$^{32}$P ATP (NEN), annealed with its complementary oligonucleotide, treated with limiting amounts of dimethyl sulfate, and then used in a preparative mobility shift assay. Dimethyl sulfate methylates N-7 of guanines in the major groove of a DNA double helix, interfering with protein binding at this site (Maxam, A. M. and Gilbert, W., *Proc. Natl. Sci. USA* 74:506–564 (1977). Partially methylated DNA was subjected to a preparative mobility shift assay, and DNA bound in complexes A and A* as well as unbound DNA subjected to cleavage with piperidine. Complexes A and A* made identical contacts on 2 G residues within the binding region (bp −62 and −68). The same preparation of affinity purified Sp1 used in an EMSA made precisely the same 2 contacts. Similar experiments performed with DNA end labeled on the complementary noncoding oligonucleotide demonstrated that complexes A and A* made identical contacts on 4 G residues within the binding region at bp −63 and at bp −61 to −59. These results suggest that complexes A, A*, and affinity purified Sp1 bind this site in a similar manner, supporting the hypothesis that A* represents a derivative of complex A (Sp1 ).

Example 11 - The Sp1 site is essential for Cd11b promoter activity

After identifying both the Sp1 binding site in the CD11b promoter and a 2 bp mutation, which no longer binds Sp1 , it was determined that mutation of the Sp1 site entirely accounts for the loss of promoter activity seen in linker scanning mutations −65/−55, −55/−45, −45/−35 and −75/−45 (see FIG. 10). The same 2 bp mutation of the Sp1 site at bp −60 and −61 was introduced into the 412 bp promoter, which has maximal activity in transient transfection assays (Pahl, H. L. et al., *Blood* 79:865–870 (1992)). Both the wild type and the mutant construct were then transiently transfected into U937 and HeLa cells. Transfections were performed as described in Example 7, above. The wild type 412 bp CD11b promoter or the promoter carrying a 2 bp mutation in the Sp1 site (Table III) were placed in front of a luciferase reporter gene and transiently transfected into macrophage (TPA induced U937) or cervical caracinoma (HeLa) cells. Transfections were carried out in duplicate and the average and standard error relative to the wild type 412 bp promoter in U937 cells (100% activity) of four experiments is shown. The results of this assay are shown in FIG. 10. Luciferase activity is reported in relative light units (RLU) and results are normalized for transfection efficiency with a cotransfected growth hormone plasmid. Background luciferase activity, obtained from transfection of the promoterless pXP2 parent plasmid, was 280 RLU.

Figure 11:
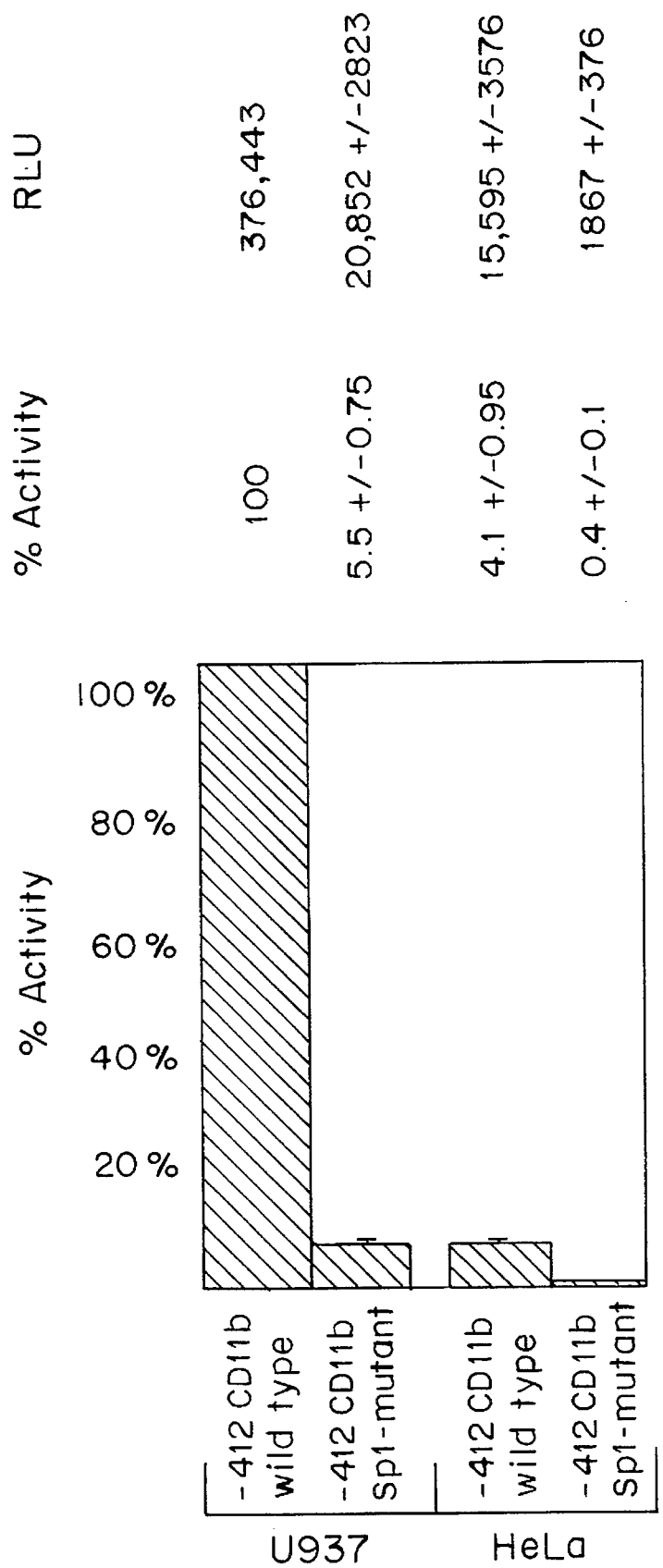
FIG. 11 is a schematic representation of the effect of mutation of the Sp1 site on CD11b promoter activity in HeLa and TPA induced U937 cells.

The 2 bp mutation at bp −60 and −61 cause an 18 fold decrease over wild type CD11b promoter activity in U937 cells. FIG. 11 shows the effect of mutation of the Sp1 site on CD11b promoter activity in HeLa and TPA induced U937 cells. The average and standard error relative to the 412 bp CD11b promoter in U937 cells of four experiments is shown. In HeLa cells, where the CD11b promoter is significantly less active, mutation of the Sp1 site decreased the low-level CD11b promoter activity 10 fold (FIG. 11). The strong effect of this mutation in the context of the entire 412 bp promoter indicates that the Sp1 site is essential not only for the activity of the 92 bp promoter, but that there are no other factors present in the 412 bp promoter which can compensate for the loss of promoter activity following mutation of the Sp1 site. In particular, the Sp1 consensus site at bp −100, which does not bind Sp1 in EMSAs cannot replace the function of the Sp1 binding site at bp −60.

Figure 12:
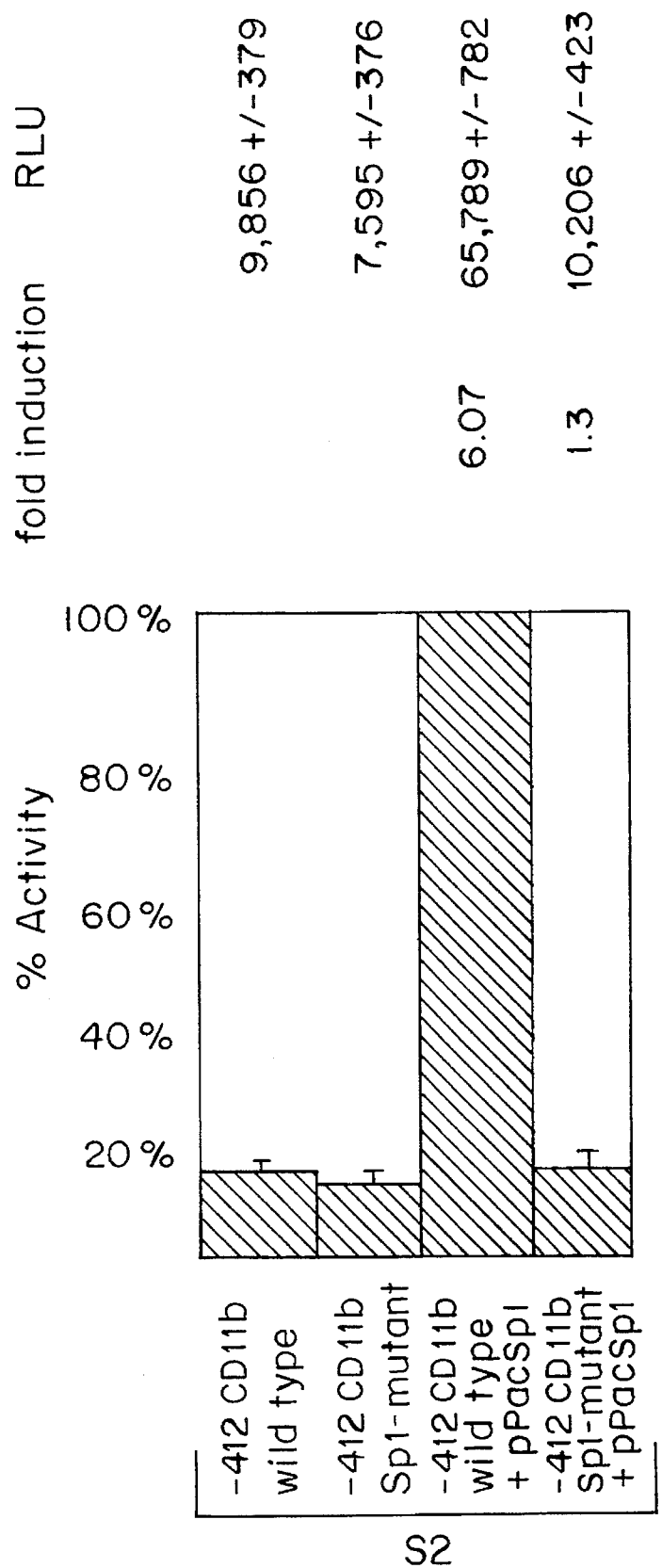
FIG. 12 is a schematic representation of Sp1 stimulation of transcription of the CD11b promoter at the −60 bp site in transactivation assays.

To demonstrate directly that Sp1 can bind to and activate the CD11b promoter, CD11b reporter constructs were cotransfected with an Sp1 expression vector (pPacSp1 ) into Drosophila Schneider (S2) cells, which, unlike most mammalian cells, lack endogenous Sp1 . The Drosophila Schneider cell line S2 was grown in Schneider medium (Sigma) supplemented with penicillin, streptomycin, and 10% heat inactivated fetal calf serum (Hyclone). For transactivation assays, S2 cells were transfected using calcium phosphate coprecipitation as described (Mangelsdorf, D. J. et al., *Nature* 345:224–229 (1990)), with the following DNA: 10 μg of reporter vector (the reporter vector comprising either the wild type −412 CD11b promoter or the promoter containing a 2 bp mutation (bp −60 and −61) in the Sp1 site, operatively linked to a luciferase reporter gene (Pahl, H. L. el al., *Blood* 79:865– 870 (1992)) (Table III)); 3 μg of the Sp1 expression vector pPacSp1 , containing the C-terminal 696 amino acids of Sp1 in a Drosophila actin promoter expression construct (Courey, A. J. and Tjian, R., *Cell* 55:887–898 (1988)); 10 μg of a plasmid containing the CMV promoter directing growth hormone expression (Pahl, H. L. et al., *Exp. Hematol.* 19:1038–1041 (1991); and KS+ pBluescript (Stratagene) to a total of 25 μg of DNA. In control experiments, the pPacSp1 construct was replaced by the retinoic acid receptor α expression vector pSG5RARα (Zelent, A. et al., *Nature* 339:714–717 (1989)). Luciferase assays were performed 14 hours after transfection as described (Pahl, H. L. et al., *Exp. Hematol.* 19:1038–1041 (1991). The results of this assay are depicted at FIG. 12. In the figure, fold induction represents RLU of wild type or mutant CD11b reporter plasmid in the presence of cotransfected SP1 divided by that obtained in the absence of Sp1 . The data in this figure represent the mean and standard error of three experiments.

When the pPacSp1 construct was cotransfected with the wild type −412 by CD11b reporter construct, luciferase activity increased 6 fold (FIG. 12). When the 2 bp mutation at bp −60 and −61 (Table III) was introduced into the 412 bp CD11b promoter, or when a retinoic acid receptor α expression plasmid was cotransfected with the wild type CD11b luciferase reporter, no increase in luciferase activity was seen in the absence of the pPacSp1 construct. These results indicate that the expression of the Sp1 protein and an intact Sp1 binding site at bp 60 and 61 were specifically necessary for an increase in luciferase activity. These observations and the data obtained in EMSAs indicate that Sp1 binds to and activates the CD11b promoter, and, additionally, that Sp1 binding is essential for Cd11b promoter activity.

Example 12 - Sp1 binds the CD11b promoter selectively in myeloid cells in vivo

In order to fully characterize the Sp1 binding site, we performed in vitro and in vivo footprinting assays. In both EMSAs and in vitro footprinting assays, protein/DNA interactions occur on short plasmid derived DNA fragments in vitro and may thus not accurately reflect binding reactions occurring on promoters embedded in chromosomal structures in vivo. For example, in vitro the muscle creatine kinase promoter binds myoD when nuclear extracts from either myoblasts or myocytes are used. In vivo, however, these sites are only bound in myocytes (Mueller, P. R. and Wold, B., Cell 35:79–87 (1983)). Thus, in vivo footprinting may more accurately reflect protein/DNA binding reactions occurring on chromatin in intact cells. Therefore, occupancy of the Sp1 site was compared in myeloid (U937) and non-myeloid (HeLa) nuclear extracts or in intact cells using both in vitro and in vivo footprinting.

For in vitro footprinting, a 370 bp fragment extending from the EcoRI site at bp –264 of the CD11b promoter to the HpaI site at bp +106 (Pahl, H. L. et. al., Blood 79:865–870 (1992)) was subcloned into pGEM 2zf(+) (Promega, Madison, Wis.). The plasmid was digested with ECORI and HindIII to release the insert, which was radioactively labeled at the HindIII site (coding strand) or the EcoRI site (noncoding strand) using [alpha-$^{32}$P] dATP as previously described (Maxam, A. M. and Gilbert, W., Proc, Natl. Acad. Sci. USA 74:506–564 (1977)). 80 µg of HeLa or U937 cell nuclear extracts were incubated with 10 ng of DNA probe, labeled to a specific activity of 1.5 ×10$^6$ cpm/µg, and 4 µg of poly didC (Promega) in 10 mM HEPES (pH 7.8), 30 mM KCl, 12% glycerol, 5 mM MgCl$_2$, 0.5 mM dithiothreitol, 0.1 mM EDTA and 0.2 mM PMSF on ice for 30 minutes. The DNA was cleaved with 180 ng of DNase I at room temperature for 1 minutes. Reactions were terminated by the addition of 100 µl of stop solution (20 mM EDTA, 0.5% SDS, 20 mM Tris (pH 7.5), 75 µg/ml sheared salmon sperm DNA, 100 µg/ml proteinase K) and subsequent incubation at 37° C. for 30 minutes. Reactions were extracted with an equal volume of phenol:chloroform, ethanol precipitated, and products analyzed on a 6% denaturing polyacrylamide gel. Chemical sequencing reactions 920) of the same DNA were used as size standards.

For in vivo methylation studies in cell lines, 10$^8$ uninduced or TPA induced (24 hours at 3×10$^{-8}$ M) U937 cells or HeLa cells were pelleted by centrifugation at 500 ×g for 5 minutes and resuspended in 2 ml of RPM1 medium. Human monocytes and lymphocytes were purified from the peripheral blood of normal donors by Ficoll-Hypaque density gradient centrifugation and separated by adherence to plastic. Cells were exposed to 0.5% (v/v) dimethylsulfide (DMS, Sigma) for 4 minutes at room temperature and DNA extracted as previously described (Tsai, S.-F. et al., Genes and Development 5:919–931 (1991). In vivo footprints were visualized using the I.M-PCR procedure (Mueller, P. R. and Wold, B., Science 246:780–786 (1989)). The universal linker used in this amplification method is composed of two oligonucleotides: linker oligo 1: GAATTCAGATC (SEQ ID NO: 5); linker oligo 2: GCGGTGACCCGGGAGATCT-GAATTC (SEQ ID NO: 6). The specific oligonucleotides from the CD11b promoter region coding strand were as follows: oligo 1, used for first strand transcription, bp –196 to –172 of the CD11b promoter: GTGACAAATGGCAC-CTTTTGGATAG (SEQ ID NO: 7); oligo 2, used for PCR amplification, bp –156 to bp –132: AAGTTTGGGTCAG-GAAGCTGGGGAG (SEQ ID NO: 8); and oligo 3, kinased with [gamma-$^{32}$P] ATP (NEN) and used in primer extension for visualization of PCR products, bp –149 to bp –124; GGTCAGGAAGCTGGGGAGGAAGGGTG (SEQ ID NO: 9). Specific oligonucleotides for the CD11b noncoding strand were as follows: oligo 1, used for first strand transcription, bp +108 to +84: TTAACAGAAGGACTCT-GAGAGCCAT (SEQ ID NO: 10); oligo 2, used for PCR amplification, bp +80 to bp +56: TGGAAGGAGCCA-GAACCTGGAAGGA (SEQ ID NO: 11); and oligo 3, kinased with [gamma-$^{32}$P] ATP (NEN) and used in primer extension for visualization of PCR products, bp +78 to bp +52: GAAGGAGCCAGAACCTGGAAGGAGGTG (SEQ ID NO: 12).

All oligonucleotides were purified by electrophoresis on 15% nondenaturing acrylamide gels followed by purification using Elutip-D (Schleicher and Schuell) columns. Autoradiographs exposed in the linear range of the film were scanned with an LKB XL laser densitometer. LM-PCR extensions stop at C residues, because the template ends at a methylated and cleaved complementary G residue; the footprinting gel shows bands at sequences corresponding to the presence of cytosines in the sequence of one strand, but implies methylation at the corresponding guanosine residues on the complementary strand.

The results of the in vitro footprinting analysis show that, sequences between bp –55 and –86 on the coding strand and bp –52 and –73 on the non-coding strand are protected from DNAse I digestion when incubated with either U937 or HeLa cell extracts.

In contrast to the results observed in vitro, only U937 cells show protection from DMS methylation between bp –54 and –70 in vivo; no in vivo footprint is seen in HeLa cells, in which the pattern generated precisely corresponds to that produced by naked genomic DNA. This in vivo binding activity is present in both uninduced U937 cells and in U937 cells induced toward monocytic differentiation with TPA. In addition, the myeloid specific in vivo binding is observed in peripheral blood monocytes, but not in lymphocytes. Therefore, the binding is observed in normal cells as well as cell lines.

It has previously been demonstrated that a 92 bp CD11b promoter construct directs "tissue specific" expression of luciferase constructs in cell lines (Pahl, H. L. et al., Blood 79:865–870 (1992)). Examination of the entire –92 bp region on the non-coding strand demonstrated only one additional site consistently protected from in vivo methylation, and this was located at bp –17 and –19, adjacent to a hypersensitive site located at bp –16. This region corresponds to the binding site for the myeloid specific transcription factor PU.1, which we have observed to bind to the –19 bp region in vitro (see Example [3]).

Analysis of the opposite (coding) strand revealed a relative reversal of the intensities of the bands at bp –68 and –70, which lie just 5' of the "core" Sp1 binding region. Because the PU.1 binding site at bp –20 does not contain any guanosine residues on this strand, no protection was observed. A second protected area was detected corresponding to the 3 G residues at bp –111 to –113; no protection was observed in this region on the non-coding strand.

Figure 13:
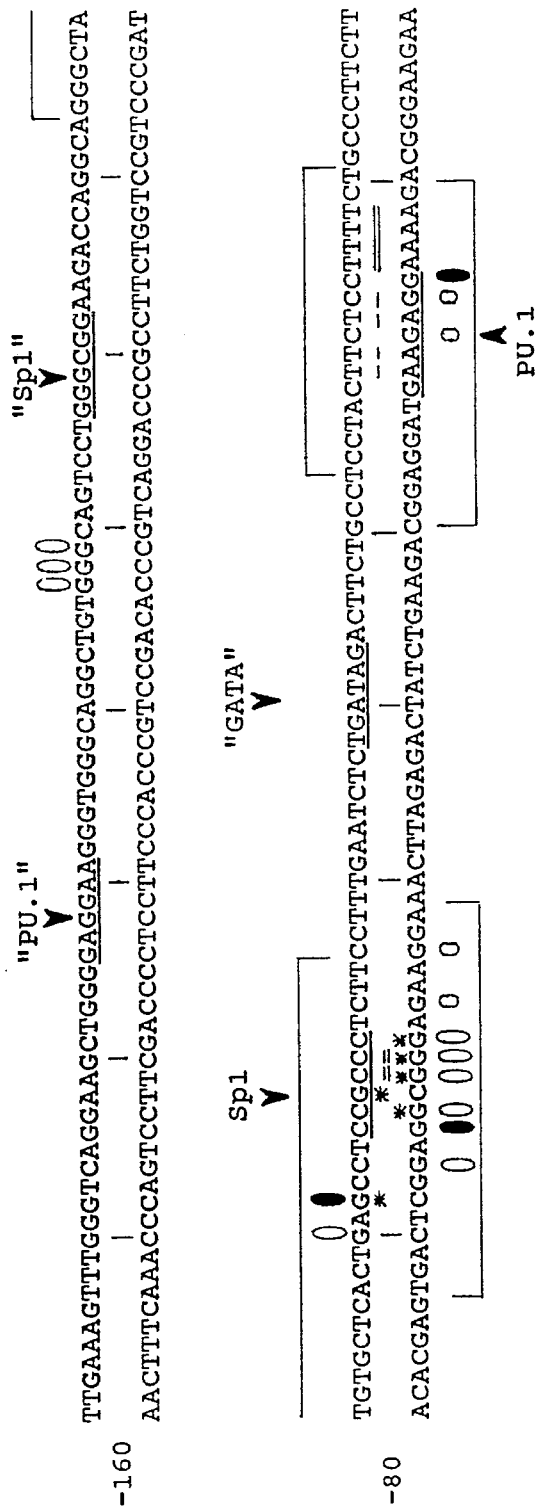
FIG. 13 represents a summary of in vitro EMSA and footprinting, methylation interference, and in vivo footprinting data, in which bp −160 to +122 of the coding strand of the CD11b promoter (SEQ ID NO: 1) and bp −160 to +80 of the non-coding strand of the CD11b promoter (SEQ ID NO: 34) are shown.

In summary, whereas the Sp1 site is bound in vitro by nuclear extracts from both CD11b expressing U937 and non-expressing HeLa cells, only CD11b expressing U937 cells and monocytes show Sp1 binding in vivo. Protection and/or hypersensitive sites were also observed at the PU.1 binding site at bp −20 and at an as yet uncharacterized site at bp −112. A summary of the in vitro and in vivo binding data is presented in FIG. 13. In this figure, the CD11b promoter sequence (Pahl, H. L. et al., *Blood* 79:865–870 (1992)) on both coding and noncoding strands is represented from bp −160 to bp +80, and from bp +81 to bp +122 on the coding strand only; bp +1 to +83 represents the 5' untranslated region, and bp +84 to bp +112 (in italics) encodes the first 10 amino acids of the leader sequence (presented in one-letter code below the DNA sequence); bp +113 to +122 represents the first 10 bases of the first intron (Fleming, J. C. et al., *J Immunol.*, in press (1993)). Vertical bars between strands (¦) denote every 10 bases, while arrowheads indicate the potential sites for DNA binding factors. The "consensus" sequences (GAGGAA at bp −130, GGGCGG at bp −100, and TGATAG at bp −40, representing potential PU.1, Sp1, and GATA factor binding sites, respectively) are underlined and labeled in quotation marks. The PU.1 and Sp1 sites do not bind their respective factors either in vitro or in vivo, and the GATA binding site does not bind its factor in vivo. Mutations in these sites do not significantly affect CD11b promoter activity. The symbols used to denote DNA binding results are presented in the box at the lower right. These results represent combined data from the experiments described above. The DNA sequence of the CD11b promoter is available in the Genbank database (Accession # M80772).

Characterization of Regulatory Sequences
Important for CD11b Promoter Activity - Sp1

Although Sp1 is universally expressed and has often been implicated in the transcription of TATA-less, "housekeeping" promoters (Dynanm W. S. and Tijan, R. *Cell* 35:79–87 (1983); Anderson, G. M. and Freytag, S. O. *Mol. Cell. Biol.* 11:1935–1943 (1991); Spanopoulou, E. et al., *Mol. Cell. Biol,* 11:2189–2199 (1991), recent evidence suggests that Sp1 expression (Saffer, J. d., et al. *Mol. Cell. Biol.* 11:2189–2199 (1991), binding affinity (Borellini, F. et al., *J. Biol. Chem.* 266:15850–15854 (1991), and post-translational modifications (Schaufele, F. et al., *J. Biol. Chem.* 265:17189–17196 (1990); Jackson, S. P. and Tijan, R., *Cell* 55:125–133 (1988)) may be modulated so as to confer tissue specific and developmental regulation (Alemany, J. et al., *Biochem. and Biophys. Res. Comm.* 183:659–665 (1992) on target genes. Moreover, levels of Sp1 expression vary greatly between tissues. Developing hematopoietic cells contain among the highest levels of Sp1 mRNA and protein (Saffer, J. D. et al., *Mol. Cell. Biol.* 11:2189–2199 (1991). Furthermore, Sp1 is phosphorylated and differentially glycosylated in various cell types, allowing additional modulation of activity (Schaufele, F. et al., *J. Biol. Chem.* 265:17189– 17196 (1990); Jackson, S. P. and Tijan, R., *Cell* 55:125–133 (1988). The CD11b promoter, like the tissue plasminogen activator promoter and other promoters regulated by the Sp1 transcription factor, does not contain a TATA box (Pahl, H. L. et al., *Blood* 79:865–870 (1992); Darrow, A. L. et al., *Mol. Cell. Biol.* 10:5883–5893 (1990); Spanopoulou, E. et al., *Mol. Cell. Biol.* 11:2216–2228 (1991)). However, unlike certain other TATA-less, "housekeeping" promoters, the CD11b promoter is highly regulated, both developmentally and in a tissue specific manner (Hynes, R. O., *Cell* 48:549 (1987).

Results herein presented demonstrate that an Sp1 site at bp −60 of the myeloid specific CD11b promoter is essential for promoter activity. It is interesting that the sequence 5' CCGCCC 3', which occurs twice in the CD11b promoter (at bp −60 and bp −100), only binds Sp1 at bp −60. In vivo footprinting implicates additional base pairs outside the CCCGCC consensus in contacting Sp1. These are not shared by the site around bp −100 (FIG. 13 and FIG. 16), and may thus be essential for Sp1 binding.

Although this Sp1 site is bound in vitro by nuclear extracts from either myeloid (U937) or non-myeloid (HeLa) cells, in vivo the Sp1 site is only occupied in CD11b expressing myeloid cells. Chromatin structure may play a role in this differential binding of Sp1. In vivo, the Sp1 site in the CD11b promoter may be inaccessible in non-myeloid cells. However, in myeloid cells, binding of tissue specific factors such as PU.1 may render the site accessible to Sp1 binding.

Although Darrow, A. L. et al. *Mol. Cell. Biol.* 10:5883–5893 (1990) have implicated Sp1 in the retinoic acid induced expression of the tissue plasminogen activator gene (Darrow, A. L. et al. *Mol. Cell. Biol.* 10:5883–5893 (1990)), and expression of the myeloid surface antigen CD11b, like tissue plasminogen activator, is induced by retinoic acid, we see no change in Sp1 binding in vitro or in vivo following differentiation of U937 cells induced with either retinoic acid or TPA. In addition, mutation of the Sp1 site does not abrogate either retinoic acid or TPA induced up-regulation of CD11b promoter activity following transient transfection. This suggests that Sp1 does not mediate the increase in CD11b expression and transcription rate observed after monocytic differentiation of U937 cells (Pahl, H. L. et al., *Blood* 79:865–870 (1992)).

Example 13 - Models of Granulocyte/Monocyte
Differentiation: Murine Embryonal Stem (ES) Cells
and Transgenic Mice The previous Examples have utilized and been aided by the use of myeloid leukemic cell lines, such as HL-60, U937, and PLB-985, which differentiate in response to retinoic acid and serve as models of myeloid differentiation. However, there are now a number of models, using non-leukemic cells, which can be used to confirm and extend results observed in leukemic cell lines, described above. In particular, these systems can be used to look at events that occur as stem cells commit toward the myeloid lineage. For example, ES cells can now be used as a model for hematopoiesis and myelopoiesis (Simon, M. C. et al., *Nature Genetics* 1:92–98, (1992); Keller, G. et al., *Mol. and Cell Biol.* 13:473–486 (1993); Wiles, M. V. and Keller, G. *Development III:259–267,* (1991)). Totipotential ES cells, which can be used to reconstitute the mouse when transplanted into recipient blastocyts, can be made to undergo in vitro differentiation in culture which recapitulates some aspects of mouse embryonic hematopoietic development. In addition, ES cells can be efficiently differentiated into myeloid cells, which upon replating in secondary cultures in the presence of M-CSF are almost exclusively macrophages. Finally, ES cells can be stably transfected with either (1) promoter/ reporter constructs, which can then be used to analyze the expression of a promoter; or (2) a gene disruption cassette, which can be used to knock out one or both copies of a target gene, including transcription factors, to look at their effect on differentiation of ES cells in vitro. A gene disruption cassette can also be used to create "knock out" mice lacking the target gene to investigate the genes role during embryonic and later development of different tissues, including tissues of the hematopoietic system. Finally, transgenic mice

Example 14 - Regulation of CD11b (and other Myeloid Genes) in Non-Leukemic Bone Marrow Hematopoietic Precursor Cells The following studies were designed to show that the same factors responsible for myeloid specific expression in leukemic tissue culture cell lines operate in non-leukemic cells and in vivo. First, a-1.7 kb CD11b promoter/β-galactosidase construct was stably transfected into ES cells, and 20 independent cell clones isolated for further study. When these cells were induced to differentiate into macrophages by plating them in methylcellulose culture in the absence of leukemia inhibitory factor (LIF) but the presence of IL-1 and IL-3, and then incubated with the β-galactosidase substrate 5-Bromo-4-chloro-3-indolyl-β-D-galactopyranoside (X-gal), bright blue staining was observed. In contrast, no staining was observed in transfected ES cells maintained in LIF, or in mock transfected cultures. When cells from embryoid bodies (selecting for macrophages in these primary cultures by allowing to proceed for 14 days, at which time macrophages are increased and erythroid cells largely gone) are then replated in secondary culture in the presence of M-CSF, almost all of the hematopoietic cells in the culture are macrophages, and again they stain bright blue when incubated with X-gal. These results indicate that the ES cell system represents a good model for studying CD11b promoter function, as well as the effect of CD11b mutants (e.g., mutants in the PU.1 and Sp1 binding sites) on promoter function. Promoter activity can be assessed more quantitively by using RNase protection assays for β-galactosidase RNA and enzymatic assays for β-galactosidase function.

Example 15 - Myeloid Cell Specific Heterologous Gene Expression in Transgenic Mice Experiments were conducted to test the activity and specificity of the CD11b promoter in transgenic mice. A DNA construct containing the −1.7 kb CD11b promoter upstream of a reporter construct which directed expression of the Thy-1.1 surface antigen was introduced into the germline of transgenic mice which express endogenous Thy-1.2 (Thy-1.1 and Thy-1.2 can be distinguished by fluorescence activated cell sorting (FACS) using monoclonal antibodies). Of the tissues surveyed, Thy-1.1 expression was only observed in cells which express murine CD11b (macrophages and neutrophils), and in the B1 (CD5+) population of B cells. Thy-1.1 expression was not observed in erythroid or T cells. Three founder animals were generated which contain a transgene in which the −1.7 kb promoter drives the expression of β-galactosidase in 72 hour thioglycollate elicited peritoneal cells, (which are predominantly macrophages); no β-galactosidase staining is observed in non-transgenic littermates. The presence of β-galactosidase RNA in these cells has been demonstrated by RNase protection assays of peritoneal macrophage RNA. β-galactosidase RNA was observed to be expressed at levels comparable to that of a highly expressed gamma-actin control probe (Simon, M. C. et al., *Nature Genetics* 1:92–98, (1992)). These results demonstrate that the CD11b promoter is active and regulated in transgenic animals, thereby enabling the study of the effects of promoter mutations in vivo.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

---

We claim:

1. A promoter of the CD11b gene comprising all or a functional portion of isolated or recombinant SEQ ID NO: 1 which directs the expression of a gene preferentially in myeloid cells.

2. A promoter of claim 1 wherein the functional portion is selected from the group consisting of: +83 to −92 of SEQ ID NO: 1, +83 to −169 of SEQ ID NO: 1, +83 to −288 of SEQ ID NO: 1 and +83 to −412.of SEQ ID NO: 1.

3. A promoter of the CD11b gene comprising an isolated or recombinant double-stranded DNA molecule wherein one strand hybridizes to all or a functional portion of the following DNA sequence (SEQ ID NO: 1):

| ATTTTTTTGT | AGAGACAGGG | TCTCTCTATG | TTGCCCAGGC |
| TGGTTTCAAA | CTCCCAGGCT | CAAGCAATCC | TCCTGCCTTG |
| GCCTCCCAAA | GTGCTGGCAT | TACAGGCGTG | AGCCACTGCG |
| CCTGGCCCGT | ATTAATGTTT | AGAACACGAA | TTCCAGGAGG |
| CAGGCTAAGT | CTATTCAGCT | TGTTCATATG | CTTGGGCCAA |
| CCCAAGAAAC | AAGTGGGTGA | CAAATGGCAC | CTTTTGGATA |
| GTGGTATTGA | CTTTGAAAGT | TTGGGTCAGG | AAGCTGGGGA |
| GGAAGGGTGG | GCAGGCTGTG | GGCAGTCCTG | GGCGGAAGAC |
| CAGGCAGGGC | TATGTGCTCA | CTGAGCCTCC | GCCCTCTTCC |
| TTTGAATCTC | TGATAGACTT | CTGCCTCCTA | CTTCTCCTTT |
| TCTGCCCTTC | TTTGCTTTGG | TGGCTTCCTT | GTGGTTCCTC |
| AGTGGTGCCT | GCAACCCCTG | GTTCACCTCC | TTCCAGGTTC |
| TGGCTCCTTC | CAGCCATGGC | TCTCAGAGTC | CTTCTGTTAA |
| CAGGTGCATG | GGG. | | |

4. A myeloid cell specific CD11b promoter-heterologous gene construct comprising all or a functional portion of SEQ ID NO: 1 and a heterologous gene, wherein expression of the heterologous gene of the construct is under transcriptional control of the CD11b promoter.

5. A myeloid cell that expresses a heterologous gene product under transcriptional control of a CD11b promoter wherein the CD11b promoter comprises all or a functional portion of isolated or recombinant SEQ ID NO: 1.

6. A myeloid cell of claim 5, wherein the CD11b promoter comprises a double-stranded DNA molecule wherein one strand sequence which hybridizes to all or a functional portion of the DNA sequence described by SEQ ID NO: 1.

\* \* \* \* \*